US009615851B2

(12) United States Patent
Neinast et al.

(10) Patent No.: US 9,615,851 B2
(45) Date of Patent: Apr. 11, 2017

(54) METHOD AND APPARATUS FOR INSERTION OF A SENSOR

(75) Inventors: Mark Neinast, Gastonia, NC (US);
Robert Bruce, Portland, OR (US); W. Kenneth Ward, Portland, OR (US);
Richard G. Sass, Portland, OR (US);
Jon Fortuna, Mechanicsburg, PA (US)

(73) Assignee: WaveForm Technologies, Inc., Salem, NH (US)

( * ) Notice: Subject to any disclaimer, the term of this patent is extended or adjusted under 35 U.S.C. 154(b) by 704 days.

(21) Appl. No.: 13/415,828

(22) Filed: Mar. 8, 2012

(65) Prior Publication Data

US 2012/0265042 A1 Oct. 18, 2012

Related U.S. Application Data

(63) Continuation-in-part of application No. 11/558,394, filed on Nov. 9, 2006.

(60) Provisional application No. 60/735,732, filed on Nov. 11, 2005.

(51) Int. Cl.
*A61B 5/145* (2006.01)
*A61B 5/1473* (2006.01)
*A61B 17/34* (2006.01)
*A61B 5/00* (2006.01)

(52) U.S. Cl.
CPC ........ *A61B 17/3403* (2013.01); *A61B 5/6849* (2013.01); *A61B 5/1473* (2013.01); *A61B 5/14532* (2013.01); *A61B 17/3468* (2013.01)

(58) Field of Classification Search
CPC ............ A61B 17/3403; A61B 17/3468; A61B 5/14532; A61B 5/6849; A61B 5/1473

USPC .......................................... 600/345–366, 309
See application file for complete search history.

(56) References Cited

U.S. PATENT DOCUMENTS

| | | | |
|---|---|---|---|
| 5,390,671 A | 2/1995 | Lord et al. | |
| 5,568,806 A | 10/1996 | Cheney, II et al. | |
| 6,001,385 A | 12/1999 | Van De Wijdeven | |
| 6,671,527 B2 | 12/2003 | Petersson et al. | |
| 6,695,860 B1 | 2/2004 | Ward et al. | |
| 6,936,006 B2 | 8/2005 | Sabra | |
| 7,025,774 B2 * | 4/2006 | Freeman | A61B 5/1411 600/583 |

(Continued)

FOREIGN PATENT DOCUMENTS

| | | |
|---|---|---|
| EP | 0709104 | 5/1996 |
| JP | 1997512200 | 9/1997 |

(Continued)

*Primary Examiner* — Navin Natnithithadha
(74) *Attorney, Agent, or Firm* — Schwabe, Williamson & Wyatt, P.C.

(57) ABSTRACT

A device and method for delivering a device such as a sensor or fluid transport structure or a fluid transport structure sensor combination into, for example, mammalian skin. Such a device allows a sensor to penetrate mammalian skin without the use of an introducer device such as a needle. A device in accordance with embodiments of the present disclosure includes a housing for attachment to mammalian skin including an exit port for receiving the distal end of a biosensor and an injection activation device including a mechanism for forcing the sensing device from a first position within the housing, through the exit port to a second position, with sufficiently high velocity to partially penetrate the mammalian skin.

18 Claims, 18 Drawing Sheets

(56) References Cited

U.S. PATENT DOCUMENTS

| | | | |
|---|---|---|---|
| 7,041,068 B2* | 5/2006 | Freeman | A61B 5/1411 600/583 |
| 7,175,642 B2* | 2/2007 | Briggs | A61B 5/1411 600/583 |
| 7,344,507 B2* | 3/2008 | Briggs | A61B 5/1411 600/583 |
| 7,351,220 B2 | 4/2008 | Chiwanga et al. | |
| 7,628,770 B2* | 12/2009 | Ethelfeld | A61B 5/6849 604/164.08 |
| 7,654,956 B2 | 2/2010 | Brister et al. | |
| 7,981,085 B2* | 7/2011 | Ethelfeld | A61B 5/14532 604/157 |
| 2002/0022855 A1 | 2/2002 | Bobroff et al. | |
| 2003/0083685 A1* | 5/2003 | Freeman | A61B 5/1411 606/181 |
| 2003/0083686 A1* | 5/2003 | Freeman | A61B 5/1411 606/181 |
| 2003/0212424 A1* | 11/2003 | Briggs | A61B 5/1411 606/181 |
| 2004/0010207 A1 | 1/2004 | Flaherty et al. | |
| 2004/0049219 A1* | 3/2004 | Briggs | A61B 5/1411 606/181 |
| 2006/0135913 A1* | 6/2006 | Ethelfeld | A61B 5/6849 604/131 |
| 2006/0142698 A1* | 6/2006 | Ethelfeld | A61B 5/14532 604/157 |
| 2007/0083131 A1 | 4/2007 | Escutia et al. | |
| 2007/0173706 A1* | 7/2007 | Neinast | A61B 17/3403 600/309 |
| 2009/0082648 A1 | 3/2009 | Ward et al. | |

FOREIGN PATENT DOCUMENTS

| | | |
|---|---|---|
| JP | 2005526560 | 8/2005 |
| WO | WO0240083 | 5/2002 |
| WO | WO2004030726 | 4/2004 |
| WO | WO2004098683 | 11/2004 |
| WO | 2006/124759 | 11/2006 |
| WO | 2007/058921 | 5/2007 |
| WO | 2011/041449 | 4/2011 |

* cited by examiner

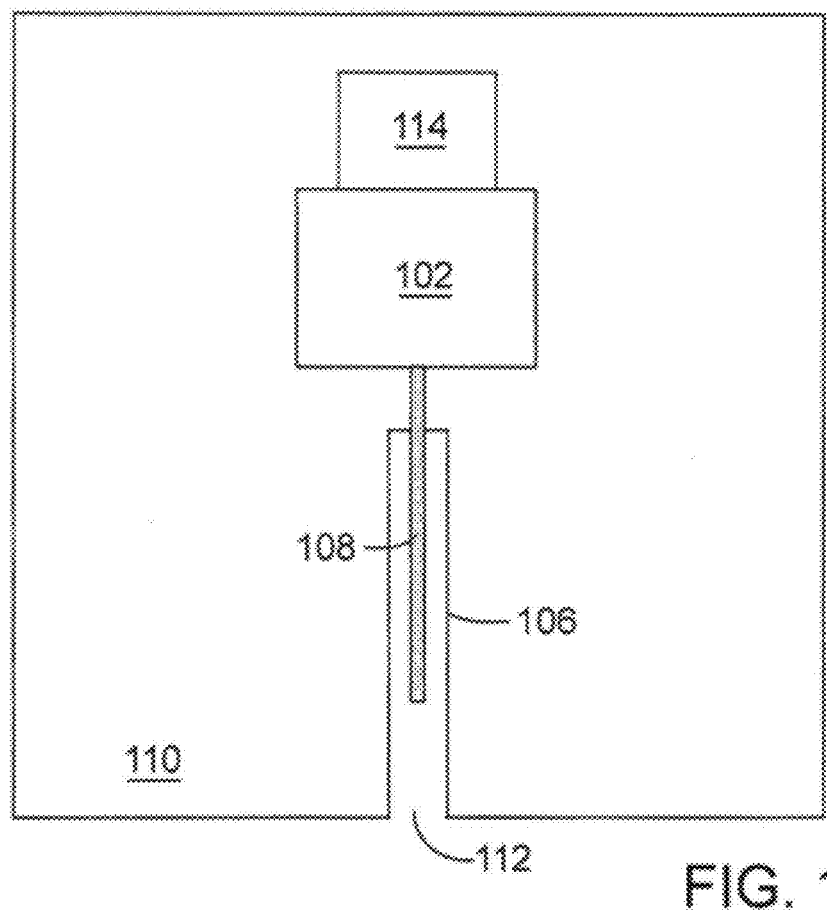
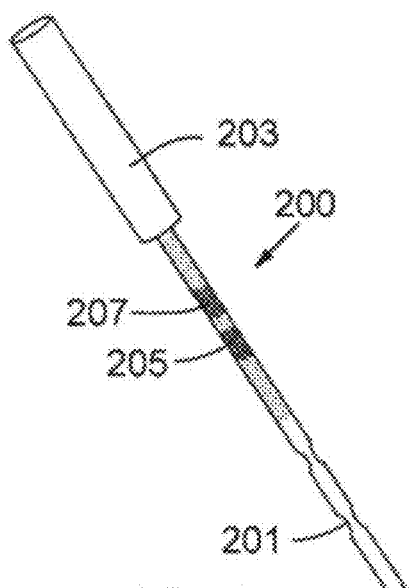
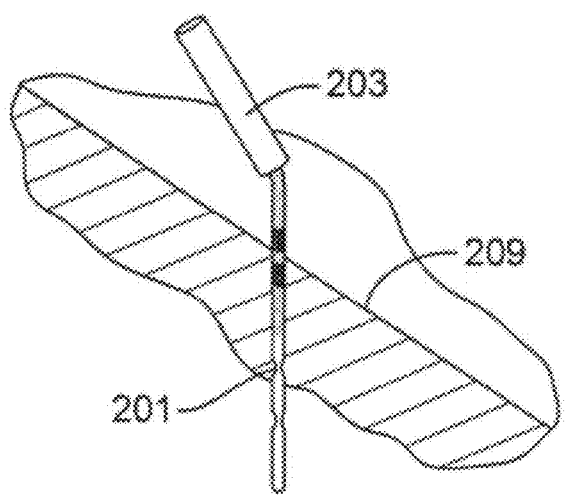
FIG. 1
FIG. 2A
FIG. 2B

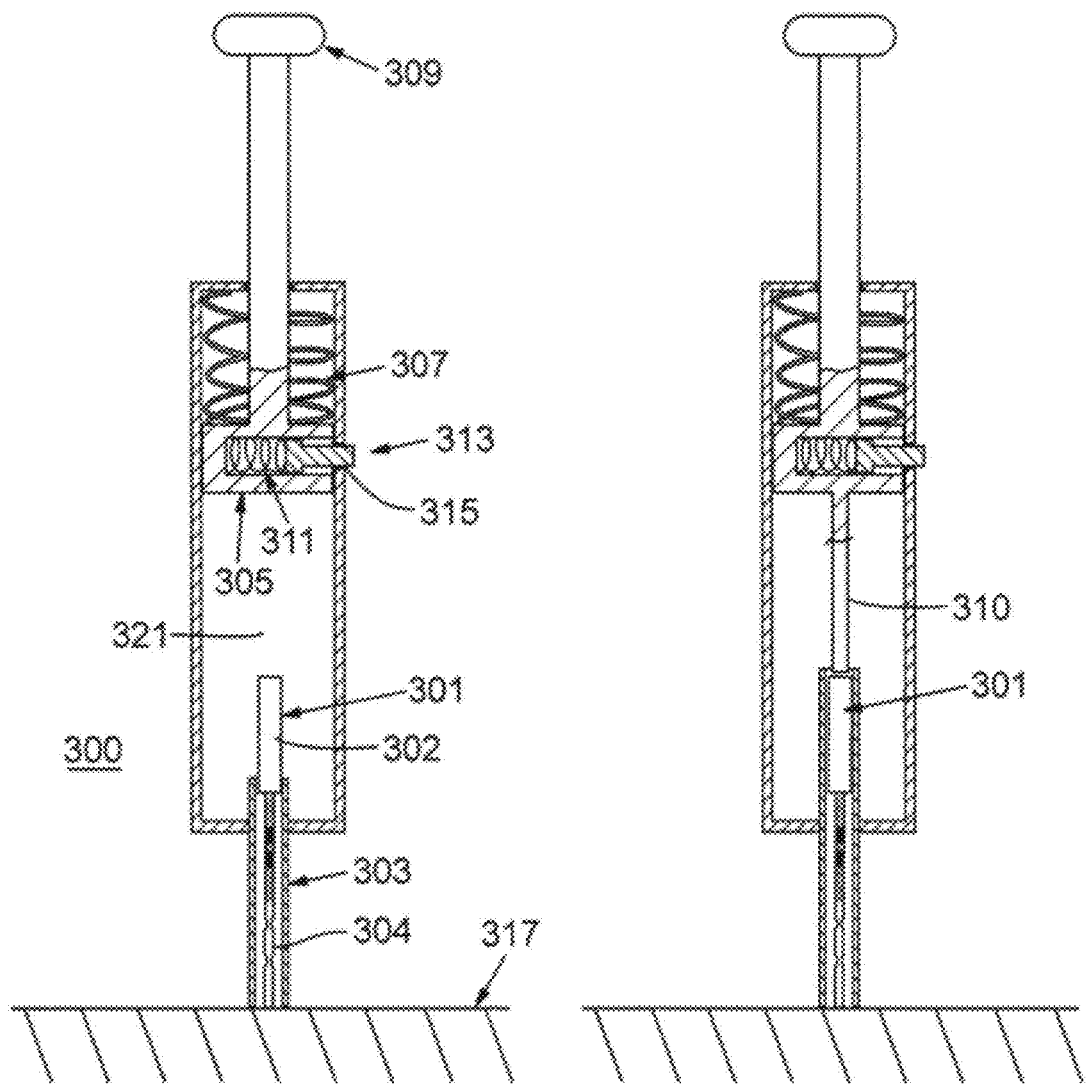

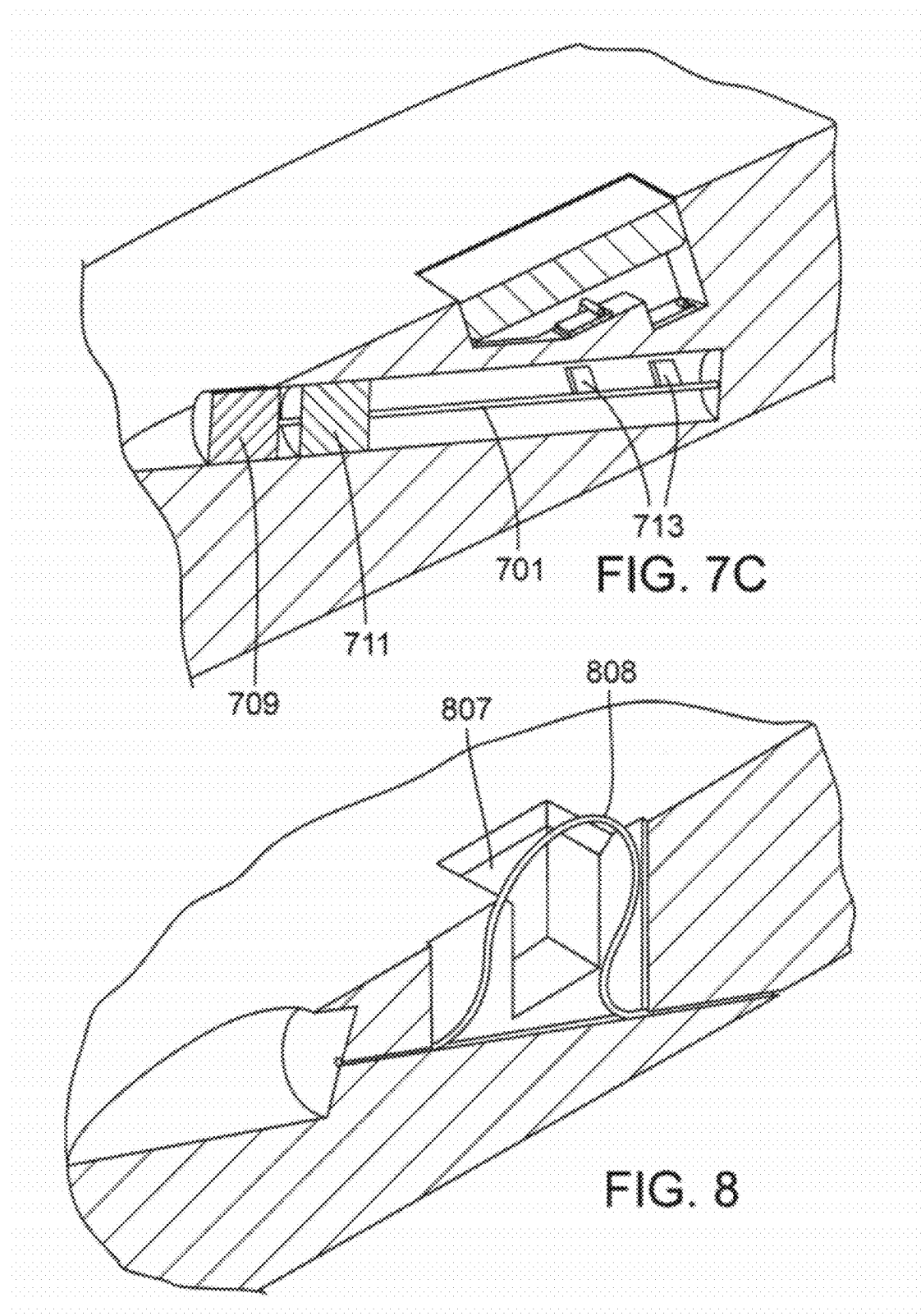

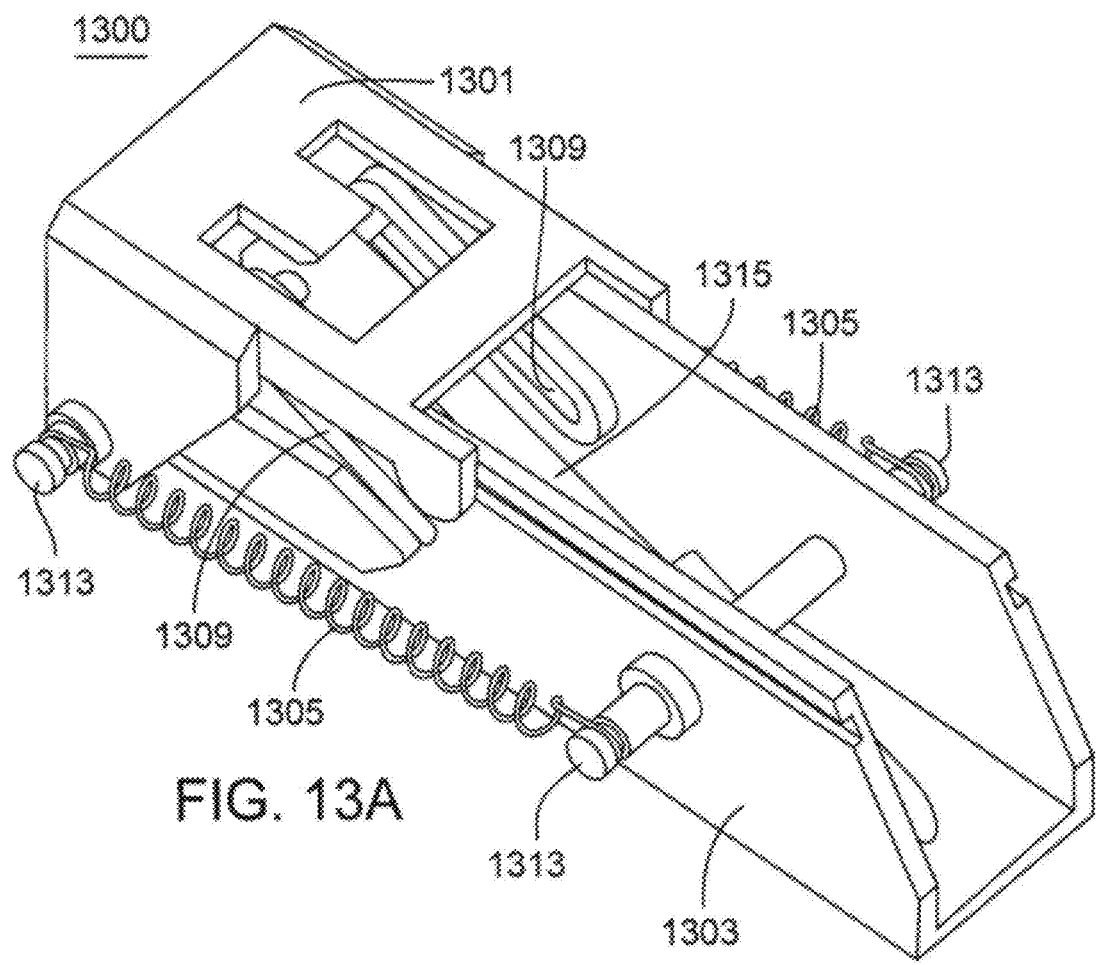
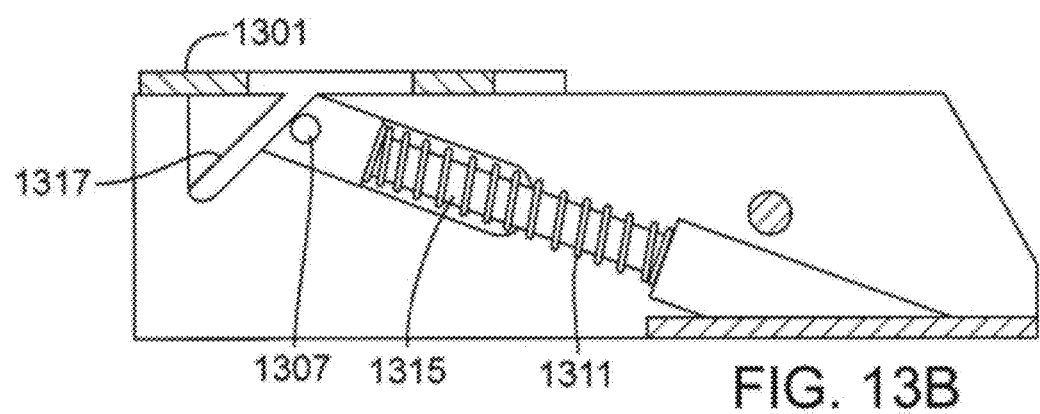

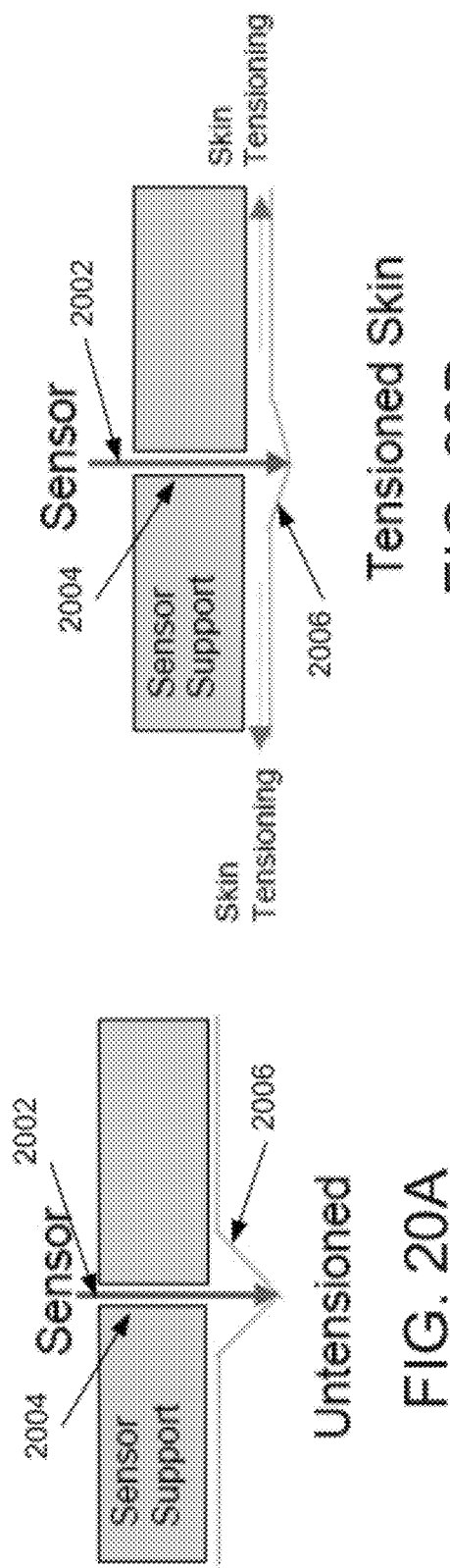
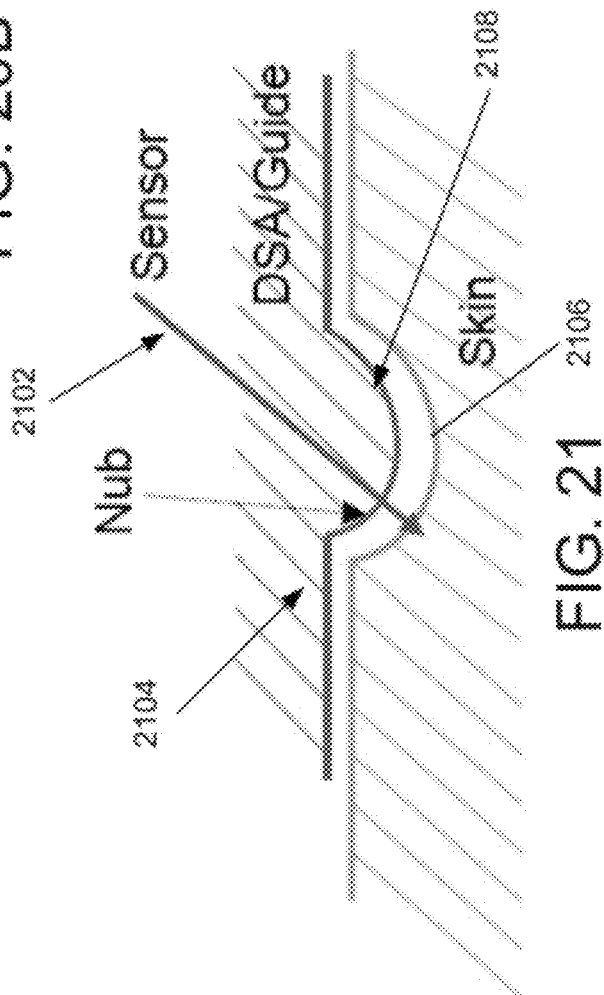
FIG. 20A Untensioned
FIG. 20B Tensioned Skin
FIG. 21

METHOD AND APPARATUS FOR INSERTION OF A SENSOR

CROSS REFERENCE TO RELATED APPLICATIONS

The present application is a continuation-in-part of U.S. patent application Ser. No. 11/558,394, filed Nov. 9, 2006, entitled "METHOD AND APPARATUS FOR INSERTION OF A SENSOR," which claims priority to U.S. Provisional Patent Application No. 60/735,732, filed Nov. 11, 2005, entitled "Method and Apparatus for Insertion of a Sensor," the entire disclosures of which are hereby incorporated by reference in their entirety.

TECHNICAL FIELD

This present disclosure relates generally to devices for delivering mechanically slender devices through skin into a body to perform various medical or physiological functions. More specifically the present disclosure relates to a method for transcutaneous placement of a soft cannula biosensor or flexible biosensor safely and automatically, without the aid of a rigid and or sharp introducer device or the resultant need for disposal of a contaminated sharp introducer device.

BACKGROUND

There are several instances of medically useful devices which are mechanically slender and flexible and are also inserted through the skin.

For example, sensors facilitate the sensing of certain conditions within a patient. Electrochemical sensors are commonly used to monitor blood glucose levels in the management of diabetes. In one scheme, an electrochemical sensor incorporating an enzyme is fabricated onto a small diameter wire. A second reference electrode is also fabricated around the wire near the sensing electrode. The sensor assembly is inserted through the skin so that it is surrounded by interstitial fluid. A portion of the sensor assembly exits the skin, remaining outside the body, where electrical connections to the sensing electrode and reference electrode may be made. A suitable electronic measuring device outside the body may be used to measure electrical current from the sensor for recording and display of a glucose value. These types of devices are described, for example, in U.S. Pat. No. 5,965,380 to Heller et al. and U.S. Pat. No. 5,165,407 to Ward et al.

In addition to electrochemical glucose sensors, a number of other electrochemical sensors have been developed to measure the chemistry of blood or other body fluids or materials. Electrochemical sensors generally make use of one or more electrochemical processes and electrical signals to measure a parameter. Other types of sensors include those which use optical techniques to perform a measurement.

In other applications, a cannula and sensor combination device is inserted through the skin to allow insulin to be introduced into the body as part of an artificial pancreas system. In these applications, a slender (small cross-section) and flexible device offers several advantages over a larger and more rigid device. Patient comfort is increased, especially during long-term insertion, and trauma at the entry site is reduced. A flexible device also is able to adjust to movement of the skin during physical activity, increasing patient comfort. In many cases these devices will remain inserted in the body for 5 to 7 days.

Although the slender and flexible nature of these devices increases patient comfort, these devices are difficult to insert through the skin. Unlike a typical hypodermic needle, these devices are too fragile and flexible to be simply pushed through the skin surface using normal force and speed. When the tip of such a device is forced against the skin, the device will bend and collapse with much less force than would be required to achieve skin penetration. Although in some cases the tip of the device may be sharpened to ease penetration, this approach is not typically adequate to assure penetration, and some devices such as tubing-based devices are not appropriate for sharpening. Also, the sharpening process adds to production cost and complexity.

As will be understood by those skilled in the art, human skin possesses biomechanical properties influenced by a relatively impenetrable outer layer, the stratum corneum, and inner layers which are more easily penetrated. These biomechanical properties cause penetration of the skin surface to present the primary challenge in introducing a relatively fragile slender, flexible device into the skin.

Current art provides several approaches for insertion of such slender flexible devices through the skin. In one case, the device is placed coaxially inside a hollow tube with a sharpened end, such as a hypodermic needle or trocar. The needle is inserted through the skin with the device inside. As a second step, the needle is withdrawn, leaving the device behind, passing through the skin into the body. See, for example, U.S. Pat. No. 6,695,860 to Ward et al. The insertion process may be painful, due to the large diameter needle, and a larger opening is made in the skin than required for passing the device alone, increasing trauma and the possibility of infection.

In a variation of this approach, the functions of the device are incorporated into a thin needle which must stay inserted into the skin. The needle provides additional mechanical strength and a sharpened point to assist in piercing the skin. However, due to its larger size and rigidity, this approach also contributes to patient discomfort for the duration of the insertion. See, for example, U.S. Pat. No. 6,501,976.

In addition, the presence of a rigid needle places mechanical constraints on the size and shape of the device housing that is attached to the surface of the skin where the device exits the skin. The needle also must be treated as a biohazard "sharp" since it is capable of transmitting disease if it should accidentally puncture the skin of another individual after being used in device insertion.

BRIEF DESCRIPTION OF THE DRAWINGS

Embodiments of the present disclosure will be readily understood by the following detailed description in conjunction with the accompanying drawings. To facilitate this description, like reference numerals designate like structural elements. Embodiments of the disclosure are illustrated by way of example and not by way of limitation in the figures of the accompanying drawings.

FIG. 1 illustrates a block diagram of an insertion device according to an embodiment of the present disclosure;

FIG. 2A illustrates an embodiment of an electrochemical glucose sensor that has been fabricated onto a length of thin, flexible wire in accordance with embodiments of the present disclosure;

FIG. 2B shows a cross-section of how an electrochemical sensor appears when inserted into skin in accordance with an embodiment of the present disclosure;

FIG. 3A shows an insertion device according to embodiments of the disclosure in which a plunger and spring combination is utilized to insert an electrochemical sensor;

FIG. 3B shows an insertion device according to embodiments of the disclosure in which a sensor is initially retracted from the skin and initially in contact with a plunger;

FIG. 7C shows a guidance concept in which spring contacts are mated to metallic guides that double as conductors;

FIG. 8 shows an embodiment of the disclosure in which energy stored in a curved sensor is utilized to provide motive force to the sensor;

FIG. 13A shows an embodiment of the disclosure in which a mechanical spring and slider combination is utilized to provide a motive force to a sensor;

FIG. 13B shows a cross sectional view of an embodiment of the disclosure in which a mechanical spring and slider combination is utilized to provide a motive force to a sensor;

FIG. 20A shows a cross-sectional view of a sensor disposed in a guidance structure during insertion with the skin untensioned in accordance with an embodiment;

FIG. 20B shows a cross-sectional view of a sensor disposed in a guidance structure during insertion with the skin tensioned in accordance with an embodiment;

FIG. 21 shows a cross-sectional view of a sensor during insertion into skin at an angle in accordance with an embodiment;

DETAILED DESCRIPTION OF DISCLOSED EMBODIMENTS

Figure 4:
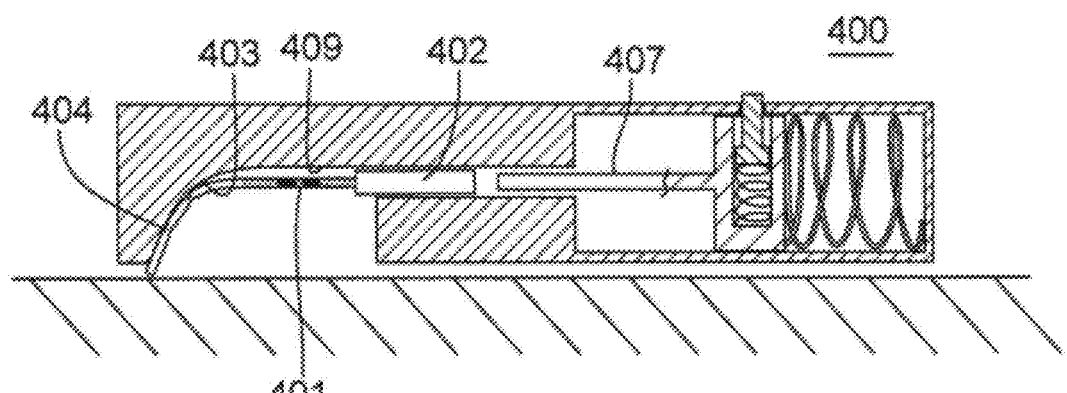
FIG. 4 shows an embodiment of the disclosure with a reduced guide and support structure.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "NB" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.).

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

Various embodiments herein provide an insertion device configured to insert an analyte sensor into skin without the aid of a sharpened introducer. An analyte sensor is also configured to be inserted into skin without a sharpened introducer.

One embodiment provides an insertion device that includes a guidance structure adapted to provide axial support to a flexible analyte sensor. The insertion device further includes an injection activation device associated with the guidance structure. The injection activation device includes a mechanism adapted to apply a high speed motive force to the flexible analyte sensor such that, when the high speed motive force is applied, the flexible analyte sensor moves at least partially through the guidance structure and at least partially passes through an exit port of the guidance structure to cause insertion of only the flexible analyte sensor into skin.

The high speed motive force is configured such that a velocity of the flexible analyte sensor at a time of insertion is in the range of 5 meters per second to 15 meters per second, such as 6.4 meters per second. In one embodiment, the high speed motive force is 11 to 53 Newtons, such as 22 Newtons.

According to one embodiment, the guidance structure is configured so that an unsupported length of the sensor is less than a buckling length of the sensor. The buckling length of the sensor is determined by a formula $Pcr=\pi^2*k/(3*L^2)$, wherein Pcr is a value of the high speed motive force applied to the sensor, k is a stiffness of the sensor, and L is the unsupported length of the sensor.

In an embodiment, the insertion device is configured to insert the analyte sensor at an insertion angle of 10 to 40 degrees with respect to a plane of the skin. For example, the insertion device includes a housing having a bottom surface associated with the guidance structure, and the guidance structure is configured so that the sensor passes through the exit port at an angle from 10 to 40 degrees with respect to the bottom surface of the housing.

In an embodiment, the insertion device further includes a tensioning structure to tension the surface of the skin so that a distance from the surface of the skin at an insertion site to the exit port is less than the buckling length of the sensor. The tensioning structure may include a nub surrounding the exit port of the guidance structure configured to indent the skin at an insertion site such that the sensor is inserted into skin at an angle that is substantially perpendicular to a plane of a local skin surface at the insertion site. According to one embodiment, the sensor is inserted with an insertion length of 12 millimeters (mm).

Another embodiment provides an analyte sensor that includes an elongate wire and an outer membrane surrounding the elongate wire at a distal end of the analyte sensor. The distal end is configured to be inserted into skin by a motive force applied to the analyte sensor without the aid of a sharpened introducer. In an embodiment, an elongate wire has a stiffness of 1.4 to 22.6 grams-force per millimeter of deflection for an unsupported length of 10 millimeters.

According to one embodiment, the wire has a diameter of 0.15 to 0.30 millimeters. The distal end of the sensor may be sharpened or may be substantially blunt.

For the purposes of describing embodiments herein and the claims that follow, the term "high speed motive force" refers to a force sufficient to drive a thin, flexible medical device into animal skin—including the relatively impenetrable outer layer, the stratum corneum, as well as the inner layers that are more easily penetrated—without substantial bending or substantial deflection of the sensor. In some embodiments, the high speed motive force is about 11 to about 53 Newtons, such as about 20 to about 22 Newtons applied to the sensor. As would be obvious to one of ordinary skill in the art, the force necessary to drive a thin, flexible medical device into animal skin increases if the medical device encounters resistance other than that provided by the surface of animal skin such as, for example, scar tissue or frictional resistance caused by a guidance structure or tube that the medical device must pass through. The term "high speed motive force" encompasses force necessary to drive the thin, flexible medical device into animal skin in situations where the medical device encounters such other resistance. Stated another way, the term "high speed motive force" encompasses any amount of motive force necessary to be applied to a thin, flexible medical device such that the sum of all forces acting on the medical device as the motive force is applied is sufficient to drive it into animal skin.

The term "actuator" refers to any of various electric, hydraulic, magnetic, pneumatic, or other means by which something is moved or controlled. The term "solenoid actuator" refers to a variety of electromechanical devices that convert electrical energy into linear or rotational motion. The term "trigger" indicates any of various electric, hydraulic, magnetic, pneumatic, or other means of initiating a process or reaction. The term "sabot" indicates a thick circular disk with a center hole.

For the purposes of describing embodiments herein and in the claims that follow, the term "axial support" means the support or bracing of a relatively straight, slender object when a motive force is applied to the object in such a way as to resist force vectors acting perpendicular to an imaginary line drawn through the device lengthwise; such support or bracing sufficient to prevent or reduce crimping, creasing, folding, or bending of the straight, slender object; or such support or bracing sufficient to enable the object to return to a relatively straight configuration after minimal bending such that the object substantially retains its original shape with minimal crimping, creasing, folding, or bending.

For the purposes of describing embodiments herein and in the claims that follow, the term "associated with" indicates that an object, element, or feature is coupled to, connected to, or in proximity to and in communication with another object, element, or feature. For example, as depicted in FIG. 1, mechanism 102 applies a high speed motive force to analyte sensor 108 such that analyte sensor 108 moves through guidance structure 106. Mechanism 102 is therefore both proximally near guidance structure 106 and in communication with guidance structure 106 and is thus "associated with" guidance structure 106.

In another example, shown in FIG. 3A, spring 307 forces plunger 305 down toward sensor 301 to drive sensor 301 through guidance structure 303. Therefore, plunger 305 and spring 307 are in communication with guidance structure 303 and are thus "associated with" guidance structure 303. Plunger 305 and spring 307 may or may not make physical contact with guidance structure 303, and may or may not be in contact when in a static position. Also in FIG. 3, spring 307 is associated with plunger 305 in that spring 307 is connected to plunger 305.

Figure 6A:
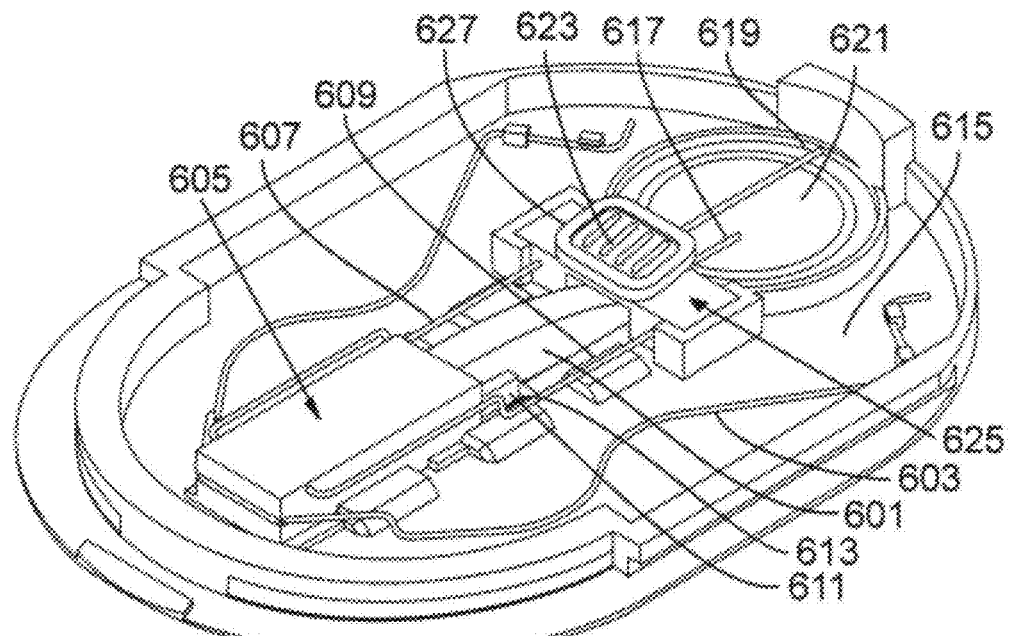
FIG. 6A shows an embodiment of the disclosure in which the components of a sensor base are exposed to view.

In another example, shown in FIG. 6A, slider 605 is coupled to guidance structure 601 and insertion spring 603 forces slider 605 to move over the top of guidance structure 601. In such a way, both insertion spring 603 and slider 605 are "associated with" curved guidance structure 601.

Figure 10:
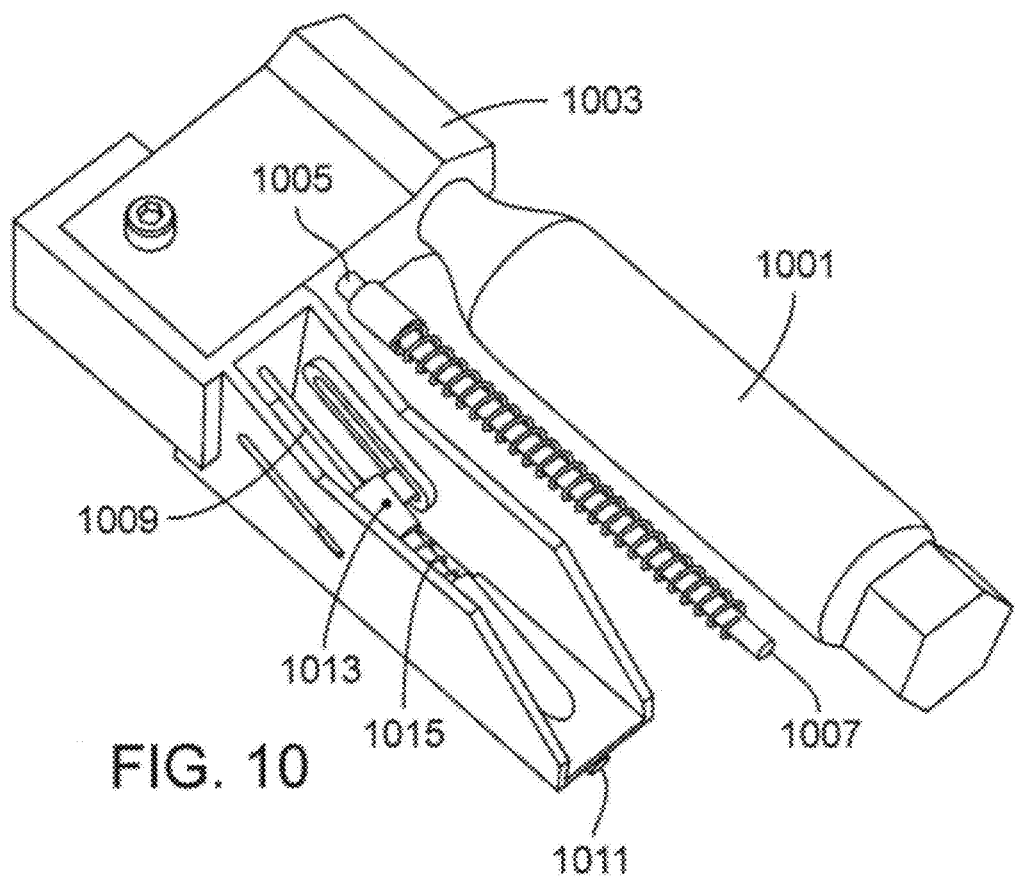
FIG. 10 shows an embodiment of the disclosure in which a $CO_2$ cartridge is utilized to provide motive force to a sensor.

In yet another example shown in FIG. 10, $CO_2$ cartridge 1001 releases $CO_2$ gas into manifold 1003 which allows the gas to pass through an internal valve (not shown) and enter hollow pin 1009 forcing rod 1011 forward striking a sensor (not shown) for insertion. Therefore $CO_2$ cartridge 1001 is in communication with a sensor (not shown) and thus "associated with" the sensor.

For the purposes of describing embodiments herein and in the claims that follow, the term "guide member" means a device that at least partially axially surrounds the analyte sensor, whether at an end or along the sensor, and is adapted to fit inside the guidance structure such that the guide member at least partially occupies at least some part of the space between the sensor and the guidance structure either during insertion, before insertion, and/or after insertion. A guide member may either provide axial support, assist a sensor in moving through the guidance structure, or both. Exemplary guide members include a sabot, a spiral of plastic, a rectangular metallic guide, an end-cap, an open cell foam plastic cylinder, and a thin plastic disk. As will be appreciated by one of ordinary skill in the art, a guide member may be made of many different materials and shaped in various geometries corresponding to the geometry of the guidance structure.

For the purposes of describing embodiments herein and in the claims that follow, the term "electrical network" means electronic circuitry and components in any desired structural relationship adapted to, in part, receive an electrical signal from an associated sensor and, optionally, to transmit a further signal, for example to an external electronic monitoring unit that is responsive to the sensor signal. The circuitry and other components include one or more of a printed circuit board, a tethered or wired system, etc. Signal transmission may occur over the air with electromagnetic waves, such as RF communication, or data may be read using inductive coupling. In other embodiments, transmission may be over a wire or via another direct connection.

An embodiment of the present disclosure includes, as shown in FIG. 1, a mechanism 102 adapted to generate a high speed motive force coupled to a guidance structure 106 which is adapted for insertion of an analyte sensor 108. Mechanism 102 is controlled by a trigger 114. In various embodiments, analyte sensor 108 is driven by a high speed motive force generated by mechanism 102 through the guidance structure and out of guidance structure opening 112. In FIG. 1, guidance structure opening 112 is shown flush with the edge of housing 110. However, in embodiments, the guidance structure opening is placed either outside of housing 110 or nested inside a larger opening of housing 110.

In an embodiment, a guidance structure is a hollow tube with a circular cross-section. A guidance structure may be linear, or curved to allow motive force to be applied to a sensor in a direction other than perpendicular to the skin in which the sensor is to be inserted. A guidance structure may be a curved hollow tube with a circular cross-section.

In various embodiments, the edge of housing 110 where opening 112 is situated is flush against skin prior to insertion. Placing the edge of housing 110 flush against the skin generates tension on the skin surface assisting in inserting the sensor without buckling or deflection of the sensor. In an embodiment in which guidance structure 112 extends beyond the surface of housing 110, the pressure of guidance structure 112 against the skin provides tension to the skin.

FIG. 2A shows an analyte sensor 200 that may be inserted according to various embodiments. In FIG. 2A, analyte sensor 200 is an electrochemical glucose sensor that has been fabricated onto a length of thin, flexible wire. A reference or ground electrode 205 and a sensing electrode 207 are incorporated into analyte sensor 200. Small diameter end 201 (proximal end) of sensor 200 may be inserted through the skin. In an embodiment, this diameter is approximately 0.25 mm or less. In an embodiment, on the larger diameter end (distal end) of sensor 200, its diameter has been increased by adding a sleeve of steel tubing 203 which increases its rigidity and facilitate electrical connections. In some embodiments, the diameter of the larger section is, for example, approximately 0.5 mm. In an embodiment, the larger diameter portion of the sensor remains outside of the body upon insertion. FIG. 2B shows a cross-section of the sensor when inserted into the skin. In some embodiments, a 10-20 mm, for example approximately 15 mm, length of sensor 200 is implanted beneath the skin.

In embodiments, a sensor may be rigid or flexible. The term "flexibility" is defined as the "amount of deflection of an elastic body for a given applied force." Flexibility is generally the reciprocal of stiffness. In some embodiments, a flexible sensor is one that can be flexed repeatedly, such as the type of flexion experienced by a subcutaneously implanted sensor in a human during normal movement, over a period of time (such as 3-7 days or more) without fracture. In an embodiment, a flexible sensor can be flexed hundreds or thousands of times without fracture.

FIG. 3A shows an insertion device in accordance with an embodiment. Sensor 301 is placed into guidance structure 303 within insertion device 300. In an embodiment, guidance structure 303 allows free passage of larger diameter end 302 of sensor 301 while providing axial support. Guidance structure 303 also provides some axial support to the smaller diameter end 304 of sensor 301, although there may be more clearance between the inside of guidance structure 303 and sensor 301 at small diameter end 304. In an embodiment, guidance structure 303 provides axial support to the sensor in order to successfully drive sensor 301 into the skin.

Insertion device 300 also contains plunger 305, compression spring 307 and a release mechanism including spring 311 and pin 313. In preparation for sensor insertion, plunger 305 is withdrawn against spring 307 using handle 309 creating tension in spring 307. The release mechanism holds plunger 305 in position. To implant sensor 301, pin 313 is forced into the body of plunger 305 through slot 315, thus compressing spring 311 and freeing plunger 305 and allowing spring 307 to force plunger 305 down barrel 321 of insertion device 300 to strike large diameter end 302 of sensor 301. Plunger 305 drives sensor 301 into position in skin 317. Upon insertion, insertion device 300 is withdrawn over the end of sensor 301 without disturbing its location in skin 317.

In an embodiment, appropriate electrical connections can be made after insertion device 300 is withdrawn. In an alternative embodiment, insertion device 300 can be integrated with a sensing device or an associated housing that has various electrical components, including electrical connections to sensor 301. In such an embodiment, the electrical components are connected to sensor 301 prior to insertion, and upon insertion, insertion device 300 is withdrawn by manipulation through a slot present in guidance structure 303 and/or in insertion device 300. In other words, guidance structure 303 and/or insertion device 300 is/are configured with a slot (straight or curved) to allow removal of either device from association with sensor 301 even while sensor 301 is electrically connected at its distal end (large diameter end) to additional electrical components.

It will be appreciated to those skilled in the art that numerous alternatives are possible for the guide and support structures, spring, plunger and release mechanism which fulfill the various purposes of embodiments for supporting the sensor and for providing a controlled impact and driving force.

It will also be appreciated that while a wire-based electrochemical glucose sensor can be used, similarly-shaped devices, such as other sensors or drug delivery devices such as small tubing used to dispense insulin or another medication can be substituted for the glucose sensor in embodiments of the present disclosure.

In an embodiment, an insertion mechanism is used only once as part of a disposable assembly. In such an embodiment, there is no need to provide a manual means to withdraw the plunger and set the release mechanism by the user, as the device is assembled with the plunger already withdrawn and the release mechanism set and ready for insertion.

To puncture the skin without damaging the sensor, a high initial impact of the sensor tip against the skin is utilized followed by a controlled driving force to complete the insertion through the softer inner skin layers. Note that an embodiment of the insertion device shown in FIG. 3A provides for a space or distance between the withdrawn plunger and the end of the sensor that will be driven.

In embodiments such as shown in FIG. 3A, the force of the spring causes the plunger to accelerate through this distance before striking the end of the sensor. The velocity of the plunger provides additional initial impact to the sensor that assists in driving it through the tough outer layer of skin quickly. In an embodiment, the force of the spring alone is sufficient to complete the insertion.

In other embodiments, the high initial impact of the sensor tip against the skin can be achieved in other ways. For example, in another embodiment, shown in FIG. 3B, sensor 301 is initially retracted from the skin and initially in contact with plunger 310. In this embodiment, sensor 301 is accelerated along with plunger 310 before impacting the skin.

In yet other embodiments, the sensor alone is accelerated by a motive force to achieve momentum causing an impact sufficient to penetrate the skin.

It will be understood by one of ordinary skill in the art that in other embodiments, means other than a spring can be utilized to provide a high speed motive force. Some examples include an electric solenoid, a shape memory alloy spring which provides an electrically initiated driving force, an associated $CO_2$ cartridge, a compressed air pump, etc.

FIG. 4 shows an embodiment of insertion device 400 with a reduced and curved guide and support means. In an embodiment, prior to insertion, sensor 401 is supported at its larger end 402. Thin distal end 404 of sensor 401 follows a curved path during insertion. However, in this case, guidance structure 409 consists primarily of a partially open region with a curved section 403 which guides and supports the sensor on only one side of sensor 401 that lies outside the radius of the arc formed by sensor 401 during insertion. It will be understood by those skilled in the art that while insertion force is applied, sensor 401 exerts a radial outward force against the supporting wall of guidance structure 409 of insertion device 400 along curved section 403. This radial force tends to support and stabilize sensor 401 without the need for a completely surrounding guidance structure.

Another feature of the embodiment in FIG. 4 is that the open region at the skin contact side of guidance structure 409 allows the sensor to be easily and completely freed from insertion device 400 when insertion is complete. In addition, in an embodiment, the open region is large enough that additional electrical connections and/or components associated with sensor 401 may be accommodated before, during, and/or after insertion.

Figure 5A:
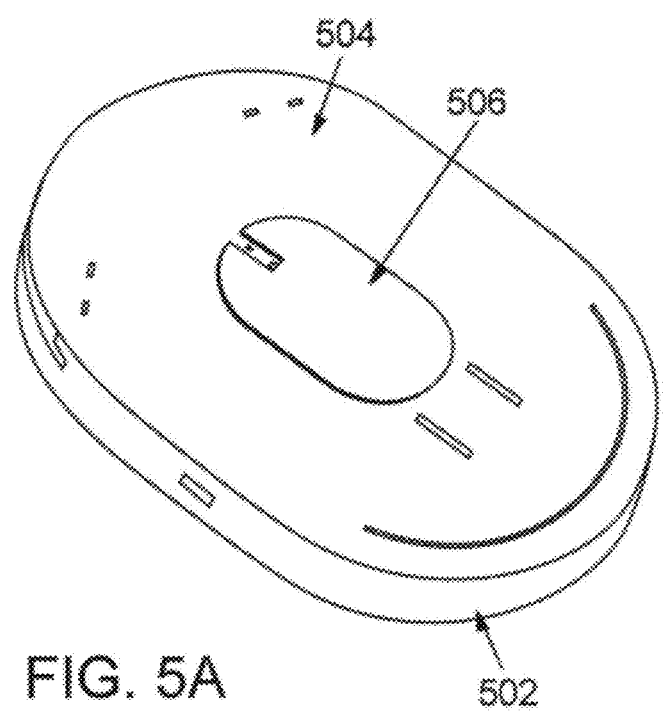
FIG. 5A shows an embodiment of the disclosure in which the insertion device includes a transmitter top and a sensor base.

FIG. 5A depicts an embodiment wherein the assembled insertion device includes a transmitter 502, a sensor base 504, which may, in an embodiment, be disposable, and a probe trigger 506. In this embodiment, a sensor and a means for supplying a high speed motive force to the sensor (not shown) are contained within sensor base 504. In an embodiment, the sensor is inserted by placing the bottom of the sensor base 504 onto the skin and pressing on the top of transmitter 502 (in a press fit, snap fit, or other type of arrangement) causing probe trigger 506 to move or otherwise be triggered causing the means for supplying a high speed motive force inside sensor base 504 to strike the sensor thereby inserting it into the skin.

The embodiment depicted in FIG. 5A includes disposable and/or reusable portions such as sensor base 504 and/or transmitter 502. Thus, in an embodiment, a resposable device is provided comprising a reusable transmitter component 502 and a disposable sensor base 504. In embodiments, other electrical components (battery, processing components, etc.) may be provided in either transmitter component 502 and/or sensor base 504.

The transmitter component can contain circuitry which may include an electrical network adapted to receive an electrical signal from an associated sensor and to transmit a further signal, for example to an external electronic monitoring unit that is responsive to the sensor signal. In embodiments, an electrical network can comprise a variety of components in any desired structural relationship, whether or not the network has a printed circuit board, a tethered or wired system, etc. In an embodiment, signal transmission occurs over the air with electromagnetic waves, such as RF communication, or data can be read using inductive coupling. In other embodiments, transmission is over a wire or via another direct connection.

Figure 5B:
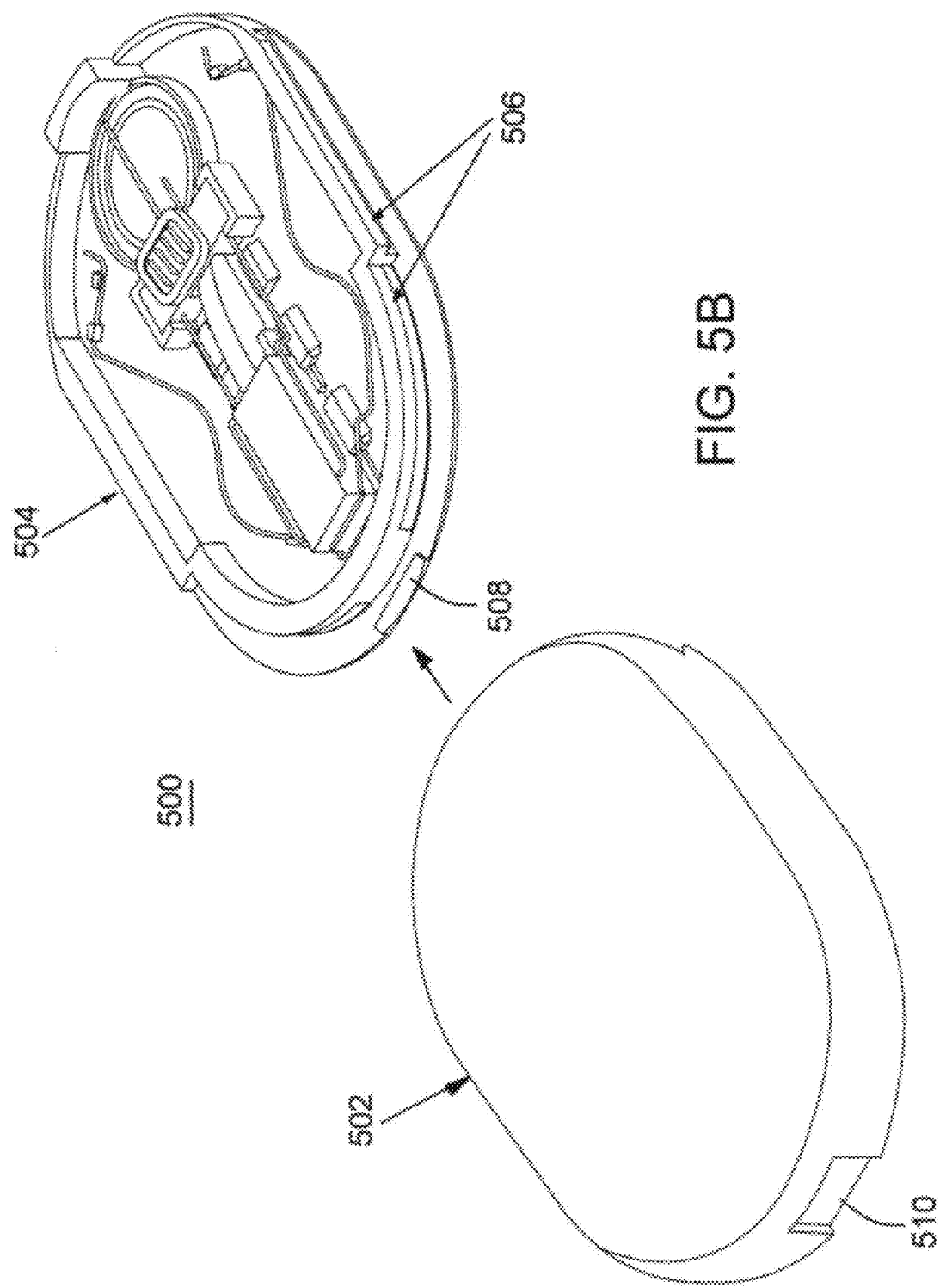
FIG. 5B shows an embodiment of the disclosure prior to the attachment of a transmitter top and a sensor base.

In an embodiment, shown disassembled in FIG. 5B, sensing device 500 is assembled by sliding transmitter 502 into grooves 506 on sensor base 504. Grooves 506 on sensor base 504 align and secure sensor base 504 and transmitter 502 together. In an embodiment, locking latch 508 secures to locking edge 510 to provide additional securing.

In an embodiment, a transmitter may be reused while the sensor base may be adapted to be used once and discarded.

In other embodiments, the sensor base and transmitter may both be reused. In still other embodiments, both may be adapted to be discarded.

In embodiments, a handtool is used to assemble the transmitter and sensor base together. The handtool is used by first placing the transmitter upside down on the handtool. The sensor base is provided with tape strip and a backing card situated along the bottom of the sensor base in place and with a protective bubble cap over the opposite face. The bubble cap may be removed from the sensor base and the sensor base may then be placed on to a sliding member of the handtool. The backing card is used to align the sensor within the handtool. Next, the sliding member may be pushed over the transmitter snapping the transmitter and sensor base together. In an alternative embodiment, the handtool has two components that hinge together rather than a sliding member. After assembly, the backing card is removed and the tool is used to position the device on a patient's body. In embodiments, by pushing on the tool, the trigger moves, activating an injection activation device and the sensor is inserted in the patient. The handtool is released by squeezing on release tabs. It will be apparent to one of ordinary skill in the art that many different embodiments of a handtool could be utilized, or, in embodiments, no handtool may be used.

In some embodiments, the means for supplying a high speed motive force is attached to the sensor base. In other embodiments, the means for supplying a high speed motive force is attached to the transmitter. In embodiments, the means for supplying a high speed motive force is in a separate handle not part of either the sensor base or the transmitter. In embodiments, such a handle is removed after insertion. Details about such a handle can be found in U.S. patent application Ser. No. 11/468,673, which describes a device that uses a handle to provide motive force to insert a sensor also employing a trocar. Although the present disclosure primarily involves a method and apparatus to insert a sensor without using a trocar or related device, details from U.S. patent application Ser. No. 11/468,673—including the handle—can be extended to various embodiments of the present disclosure.

FIG. 6A shows components of sensor base 600 in accordance with an embodiment. Curved guidance structure 601 is coupled to insertion spring 603 via slider 605 which houses the upper end of a curved probe (not shown). Leads 607 and 609 are soldered to the sensor to make electrical contact. Thus, slider 605 provides a housing for insert-molding thereby sealing the terminations and providing protection for the otherwise exposed probe.

Insertion spring 603 is attached during manufacturing and pulled back over the outermost end of slider 605. Slider 605 is kept from moving forward by two beams 611 (only one shown) which protrude from slider 605 and engage the edges of rectangular holes 613 in base surface 615 of sensor base 600. In this manner, insertion spring 603 holds potential energy and slider 605 remains stationary.

Battery leads 617 and 619 are, for example, spot welded to battery 621 and battery 621 is secured in place using a potting compound (not shown) and/or other suitable securing compound or mechanical means. All four leads 607, 609, 617, and 619 are attached to small wire springs 623 that are insert-molded into connector assembly 625. A soft rubber gasket 627 is attached to the periphery of connector assembly 625 for sealing with a corresponding contact pad on the transmitter (not shown) once the transmitter is secured into place. The connection face of connector assembly 625 is on an angle so that the contacts and sealing features do not interfere during mating and so that the total mating forces do not act to try to disengage the transmitter and sensor base 600.

Figure 6B:
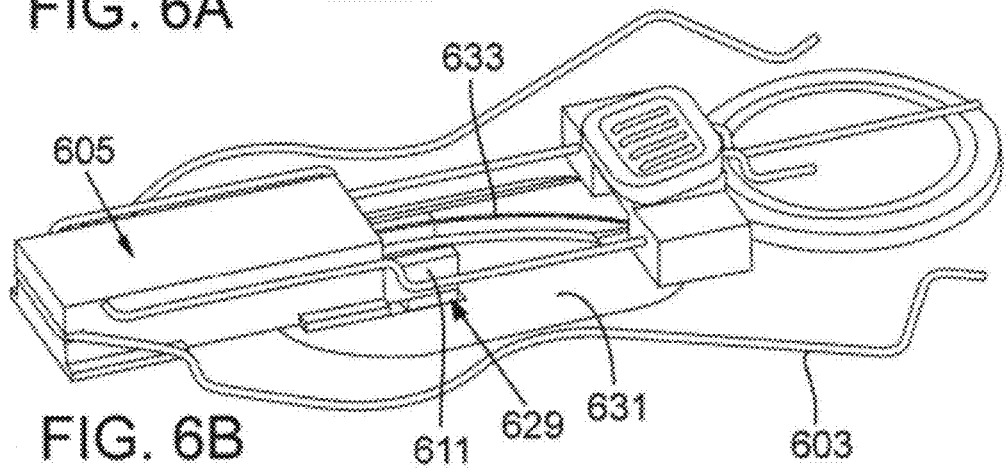
FIG. 6B shows an embodiment of the disclosure in which only some of the components of a sensor base are exposed to view.

FIG. 6B shows an exploded view of some components of sensor base 600. In this view, guidance structure 601 is omitted exposing probe 633 and riser 629 of trigger 631. In this embodiment, riser 629 is pressed upward which in turn pushes the two rectangular beams 611 upward causing them to slide against the forward edges of rectangular holes 613 (see FIG. 6A) and be released. Once released, insertion spring 603 no longer encounters resistance and causes slider 605 to quickly move forward. In so doing, curved probe 633 will pass through the curved guidance structure and partially pass through an opening (not shown) in the sensor base and may then be inserted into the skin of a patient.

In this embodiment, trigger 631 is activated by placing the apparatus on the skin of a patient and applying downward pressure causing trigger 631 and, thus, riser 629, to rise upward in relation to the device.

Figure 6C:
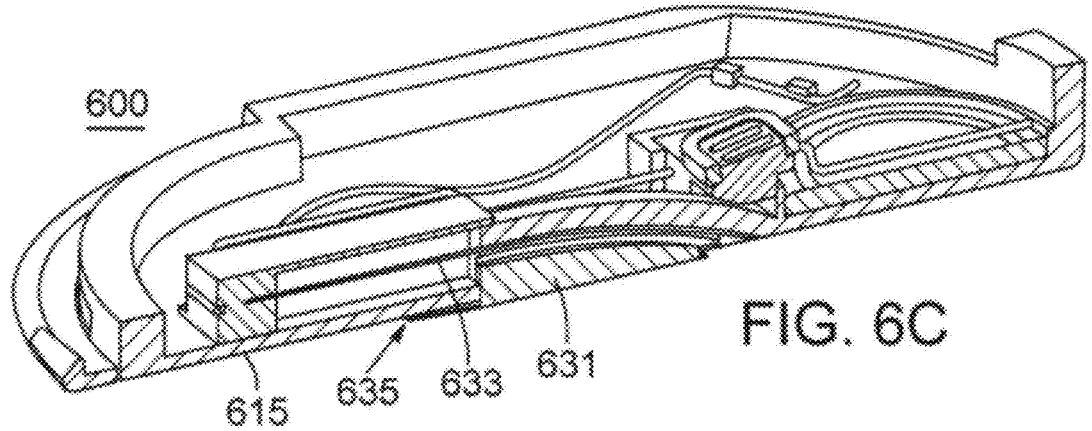
FIG. 6C shows a cross sectional view of a sensor base in accordance with an embodiment of the disclosure.

FIG. 6C depicts a cross-sectional view of sensor base 600. Here trigger 631 is more clearly shown. A curved feature on the top of trigger 631 holds probe 633 in place before insertion and helps guide curved probe 633 during insertion. Gap 635 between trigger 631 and base surface 615 close when trigger 631 is pushed up during insertion.

Figure 7A:
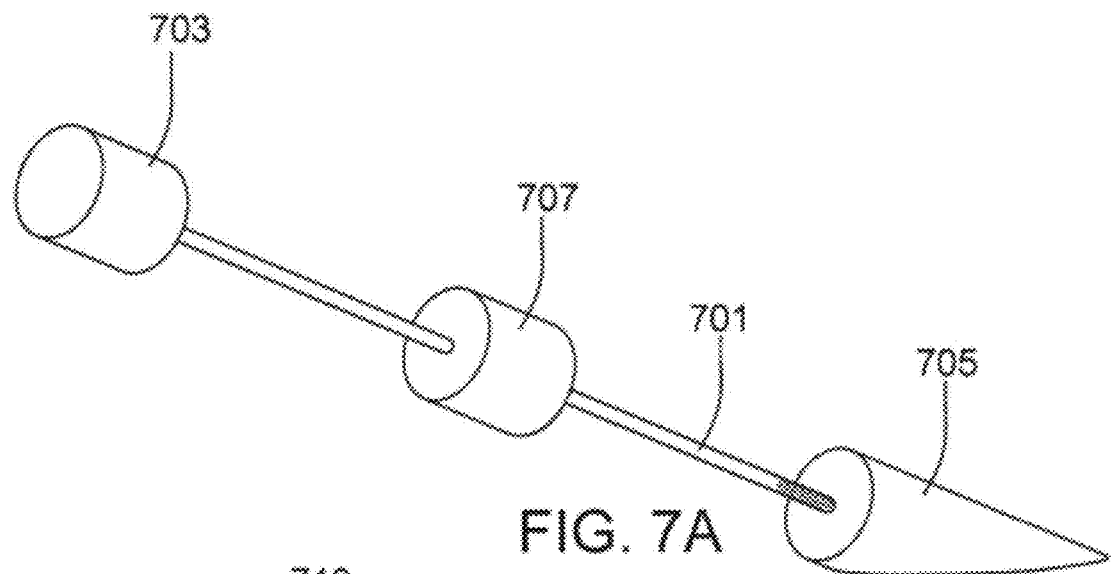
FIG. 7A shows a guidance concept in accordance with an embodiment of the present disclosure in which a sensor is guided using three plastic guides.

FIG. 7A depicts a probe guidance concept in accordance with an embodiment of the present disclosure. Sensor 701 is shown with a permanently attached top guide 703. In an embodiment, top guide 703 is insert-molded onto sensor 701. In another embodiment, top guide 703 is attached with adhesive bonding. In other embodiments, top guide 703 is ultrasonically welded. Lower end guide 705 is part of the housing body of the device (not shown). Upon insertion, sensor 701 slides within lower end guide 705 which may be a molded feature of the housing body. In another embodiment, lower end guide 705 is a separate piece bonded to the housing body during manufacturing.

Lower end guide 705 is angled to allow sensor 701 to be inserted into the skin at an angle other than 90-degrees relative to the skin. In other embodiments, sensor 701 is inserted at other angles from 0-90 degrees, including 90 degrees.

Central sabot guide 707 is free-floating and remains roughly centrally located on sensor 701 as sensor 701 is inserted into the skin. In other words, in an embodiment, central sabot guide 707 is bonded to neither sensor 701 nor the insertion device. Central sabot guide 707 prevents buckling of sensor 701 upon insertion. All components of FIG. 7 remain with the device after sensor 701 is inserted.

Although the guidance concept in FIG. 7A is shown with three guides, it will be understood by one of ordinary skill in the art that more than three guides or less than three guides can be employed to guide the sensor and prevent buckling. Although the guidance concept depicted in FIG. 7 is shown with cylindrical guides, it will be understood by one of ordinary skill in the art that other geometries could be employed including, but not limited to, rectangular geometries. In various embodiments, the guides are shaped and sized to accommodate the shape and size of the guidance structure.

It will be understood by one of ordinary skill in the art that the guides depicted in FIG. 7A may be produced from a variety of materials including, but not limited to, various plastics or metals.

In some embodiments, the central guide is composed of open cell foam plastic easily collapses during insertion and have virtually no elasticity once compressed.

In another embodiment, the central guide is a spiral of plastic with a center hole that serves to guide the probe and prevent buckling during insertion. The spiral may collapse during insertion and take up very little space when compressed. It may remain within the body of the device upon insertion of the sensor. Manufacture of the plastic spiral may be accomplished by molding or by employing a device similar to a rotini pasta extruder.

In another embodiment, the central guide is replaced by a series of thin plastic disks each with a central hole. The disks may guide the probe and prevent buckling during insertion. Upon insertion, the disks may close upon each other and take up very little space when compressed. In various embodiments, the disks are molded or stamped from a thin sheet of plastic.

Figure 7B:
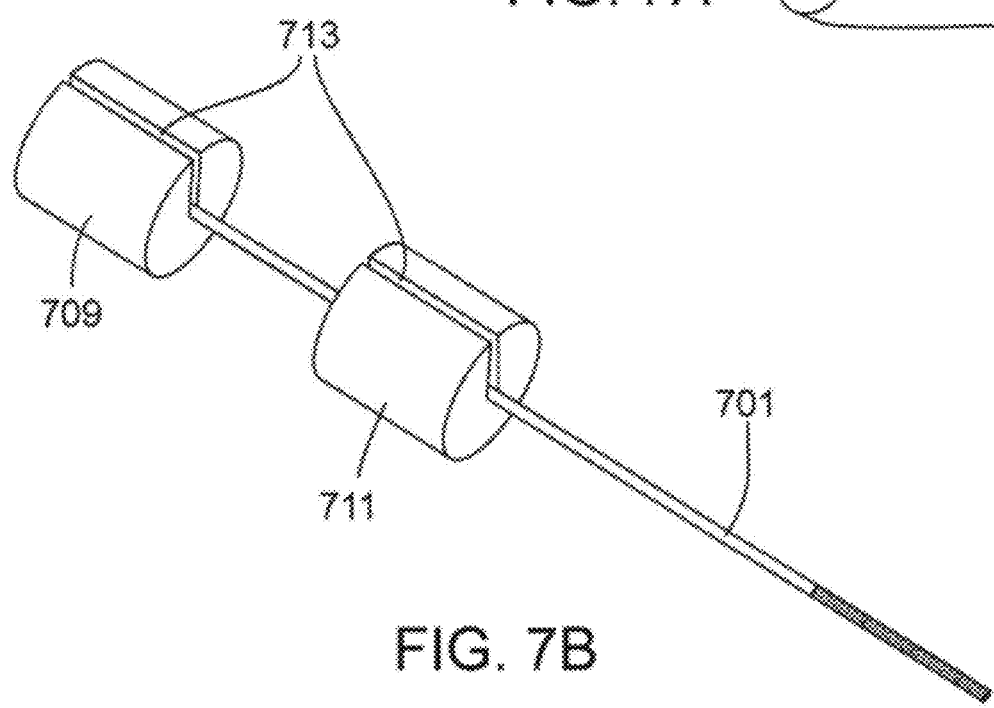
FIG. 7B shows a guidance concept in accordance with an embodiment of the present disclosure in which the sensor has attached two metallic guides that double as conductors.

In the embodiment depicted in FIG. 7B, top guide 709 and central guide 711 facilitate the making of an electrical connection to sensor 701 as well as helping to guide sensor 701 and prevent buckling during insertion. In these embodiments, the guides are made of a suitable conductive material including any number of suitable metals. In an embodiment, top guide 709 is soldered to an exposed core of the sensor (not shown) and central guide 711 is soldered to silver cladding (not shown) via grooves 713. Soldering top guide 709 to sensor 701 creates a permanent attachment to sensor 701 and allows a mechanism for applying a high speed motive force (not shown) to act directly against top guide 709 during insertion.

Referring now to FIG. 7C which shows a cross-sectional view of an embodiment of the sensor and guide design of FIG. 7B placed into an insertion device, electrical contact is made between the device and guides 709 and 711 by employing a set of leaf spring contacts 713 built into the body of the device. Contact is made near the end of the travel of sensor 701 upon insertion. In other embodiments, electrical contact is made by soldered wires that are dressed away from sensor 701 between the top and central guides 709 and 711, respectively.

FIG. 8 depicts a cross-sectional view of the bottom of an insertion device in accordance with an embodiment. Sensor 801 is shown bowed and restrained within the body of the device. The top curve of bowed sensor 801 extends slightly out of exposed opening 807. As depicted in FIG. 8, exposed opening 807 is situated on the bottom surface of the device (the surface adapted to be placed onto the skin). The device can be placed against the skin of a patient (not shown) and pressed down. Force can be applied to the top of bowed sensor 801 to force sensor 801 to straighten forcing proximal tip/end of sensor 801 into contact with the skin with enough pressure to cause sensor 801 to penetrate the skin. Sensor 801 may contain core material with sufficient elastic properties to store a sufficient amount of energy when bowed in order to generate a high speed motive force when straightened.

Figure 9A:
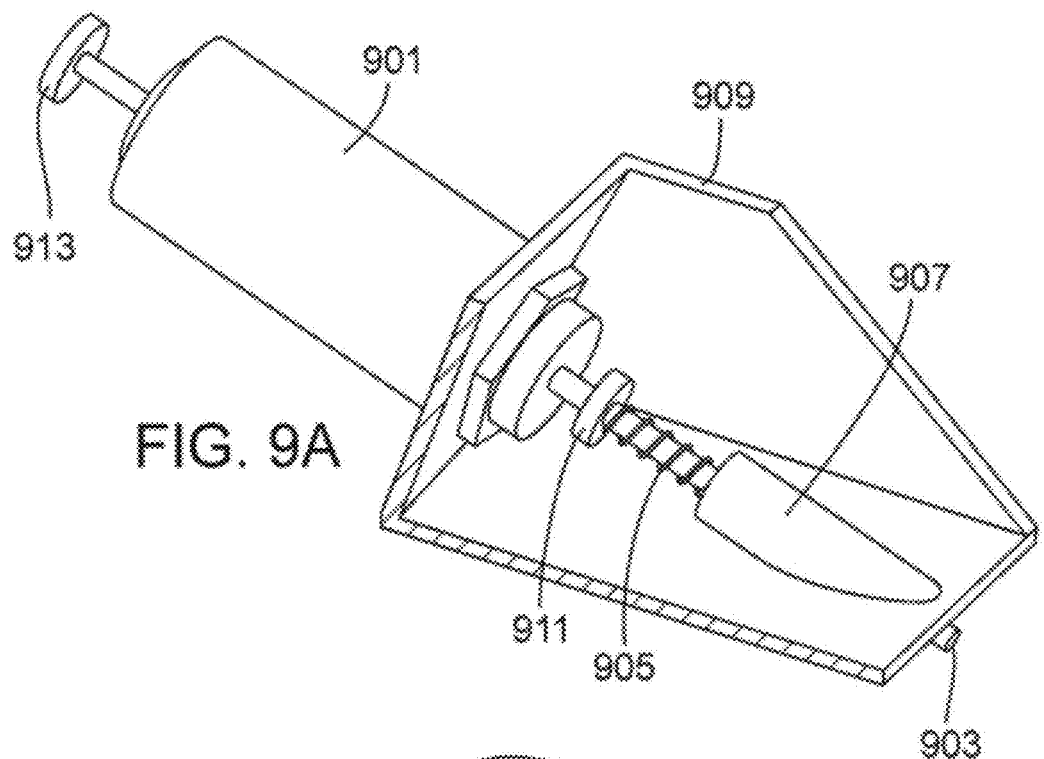
FIG. 9A shows an embodiment of the disclosure in which a linear solenoid is utilized to provide motive force to a sensor.

In various embodiments, the direct drive linear solenoid actuator design of FIG. 9A is employed to provide a high speed motive force to a sensor. In these embodiments, solenoid 901 is coupled to the main body of the device using support structure 909. Support structure 909 includes cylindrical member 907 which contains a hollow core. Solenoid shaft 903 is extended so that it also becomes an insertion rod directly impacting and providing a high speed motive force to the end of a sensor (not shown). In an embodiment, solenoid shaft 903 is partially situated in cylindrical member 907. When power is applied to solenoid 901, shaft 903 travels through cylindrical member 907 to provide a high speed motive force to a sensor for insertion. After insertion, return spring 905, situated between the end of cylindrical member 907 and shaft stop 911, causes the shaft to return to its pre-insertion position.

Figure 9B:
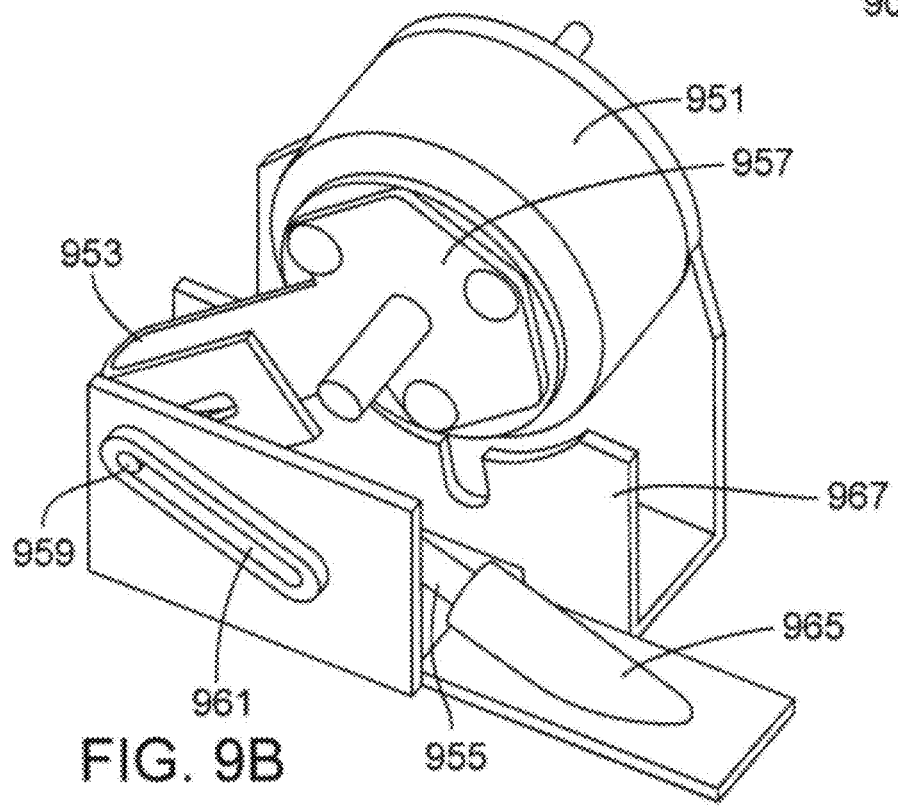
FIG. 9B shows an embodiment of the disclosure in which a rotary solenoid is utilized to provide motive force to a sensor.

In various embodiments, the rotary solenoid actuator design of FIG. 9B is employed to provide a high speed motive force to a sensor. In these embodiments, a rotary solenoid 951 is coupled to the main body of the device using support structure 967. An arm 953 is attached to the solenoid's rotating plate 957 and the far end of the arm is slotted and bent back on itself providing an opening for engaging pin 959 attached to the top end of rod 955. Whenever power is applied to solenoid 951, it turns clockwise (as oriented in FIG. 9B) which causes rotating plate 957 to rotate and pin 959 to move along linear guide slot 961. The linear motion of pin 959 causes associated rod 955 to move in a linear direction through hollow cylindrical member 965 which is part of the housing structure of the device. Rod 955 then impacts the end of a sensor (not shown) and provides a high speed motive force for insertion of the sensor.

In various embodiments, the rod returns to its original position whenever power is removed from the solenoid. In embodiments, a spring is incorporated into the solenoid by the manufacturer to ensure that it returns to the rest position whenever power is removed.

It will be appreciated by those of ordinary skill in the art that embodiments of the disclosure which utilize solenoids are not limited by the configurations depicted in FIGS. 9A and 9B. For example, the rotary solenoid embodiments depicted in FIG. 9B incorporate a cam surface rather than a rotating arm connected to rotating plate. Embodiments which use a linear solenoid actuator as in FIG. 9A incorporate intermediate components in various configurations to impact the end of the sensor rather than utilizing an elongated solenoid shaft as depicted in FIG. 9A.

FIG. 10 depicts an embodiment employing a $CO_2$ cartridge. As depicted, the head of $CO_2$ cartridge 1001 is placed into a hole in manifold 1003 and a nut behind $CO_2$ cartridge 1001 tightened causing $CO_2$ cartridge 1001 to move deeper into the manifold where a hollow pin (not shown) pierces $CO_2$ cartridge 1001 and allows the compressed $CO_2$ to enter the system. There are two internal manifold chambers (not shown). One chamber connects to $CO_2$ cartridge 1001 and the other connects to hollow pin 1009. A spring loaded valve (not shown) is located between them to initially hold back pressure from cartridge 1001 and its associated manifold chamber. Whenever spring loaded firing pin 1007 is allowed to strike valve head 1005, an internal valve (not shown) temporarily opens and an amount of gas may flow from the manifold chamber associated with $CO_2$ cartridge 1001 into the manifold chamber associated with hollow tube 1009. Gas may then enter hollow tube 1009 and force rod 1011 to move forward and strike a sensor (not shown) for insertion. As rod 1011 nears the end of travel, exhaust port 1013 travels past the end of hollow tube 1009 allowing the $CO_2$ to escape. Return spring 1015 is employed to move rod 1011 back to its original position after insertion.

Figure 11:
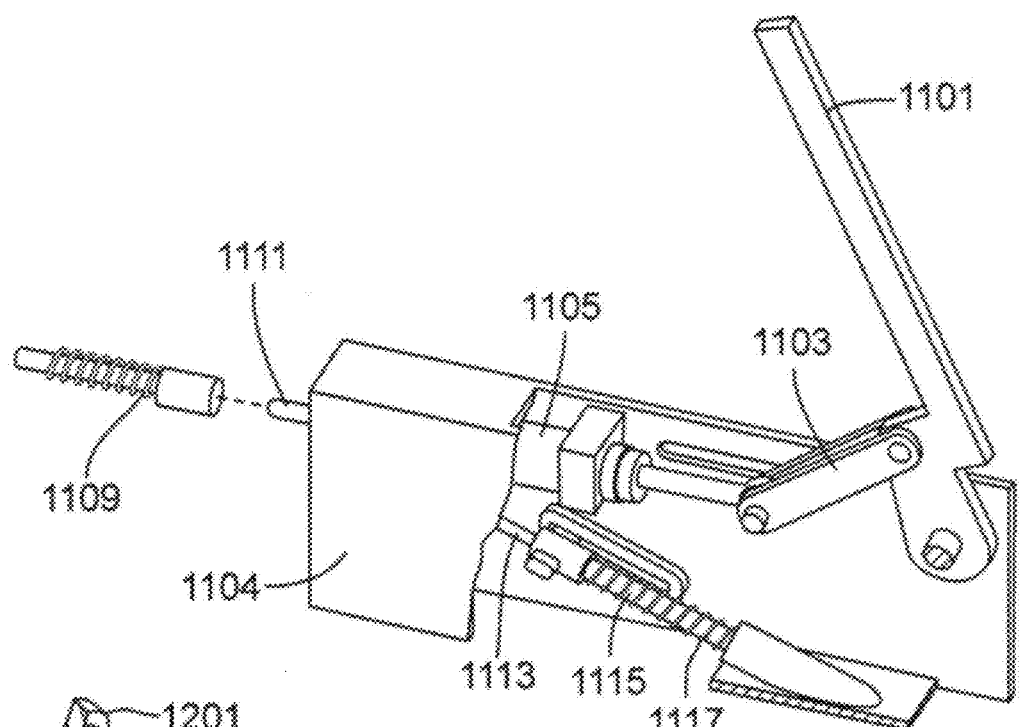
FIG. 11 shows an embodiment of the disclosure in which an air pump and piston are utilized to provide a motive force to a sensor.

An embodiment employing an air pump is depicted in FIG. 11 in a cross-sectional view. The embodiment shown in FIG. 11 employs a similar manifold system as in the $CO_2$ cartridge embodiment discussed previously. The manifold is encased in housing structure 1104. When lever arm 1101 is pulled up, air may be sucked into a manifold chamber associated with piston 1105 via a one-way valve (not shown). Pushing lever arm 1101 down moves link 1103 which is coupled to the shaft of piston 1105 which is forced into its associated manifold. The motion of piston 1105 into the manifold compresses the air that has been sucked into the associated manifold chamber on the upward stroke of lever arm 1101. When spring loaded firing pin 1109 is allowed to strike valve head 1111, an internal valve (not shown) temporarily opens and compressed air moves from the manifold chamber associated with piston 1105 into a manifold chamber associated with hollow tube 1113. Gas then enters hollow tube 1113 and force rod 1115 to move forward and strike a sensor (not shown) for insertion. As rod 1115 nears the end of travel, an exhaust port on the rod (not shown) travels past the end of hollow tube 1113 allowing the compressed gas to escape. Return spring 1117 is employed to move rod 1115 back to its original position after insertion.

Figure 12:
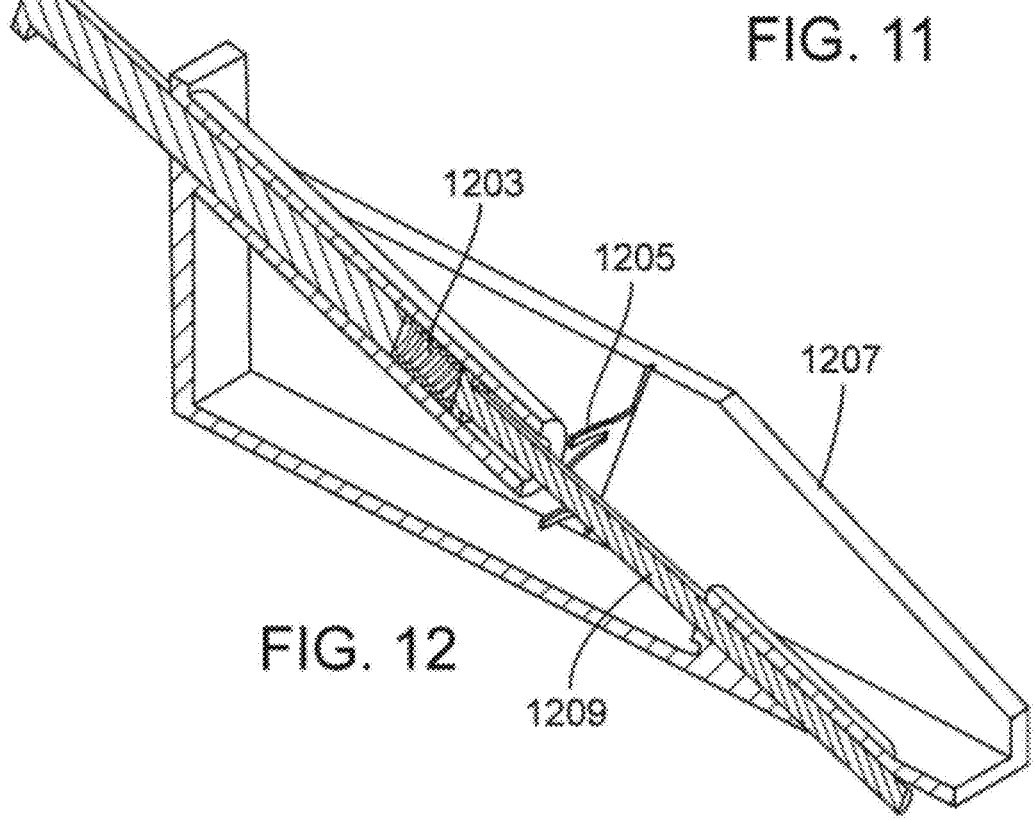
FIG. 12 shows an embodiment of the disclosure in which a mechanical spring is utilized to provide a motive force to a sensor and the activation is controlled by a separate bowed spring.

FIG. 12 depicts an embodiment employing a mechanical spring. In this embodiment, bowed spring 1205 is initially bowed upward toward button 1201 and placed into actuator frame 1207 part way along the length of rod 1209. If button 1201 is pressed, it compresses power spring 1203 against bowed spring 1205 while a cut-out in bowed spring 1205 engages a slot cut into rod 1209 to prevent the head of rod 1209 from moving forward. In an alternative embodiment, an outside ridge is employed instead of a slot on rod 1209.

At a predetermined force, bowed spring 1205 exhibits an "oil can" effect and its bow immediately reverses orientation. This action releases rod 1209 from the ridge cut into bowed spring 1205 and rod 1209 is then driven forward by the force built up in power spring 1203 which then strikes a sensor (not shown) with a high speed motive force for insertion.

FIG. 13A depicts a mechanical spring in accordance with embodiments herein. Slider 1301 is pulled back to the far end of support structure 1303 creating tension in springs 1305 which are supported by pins 1313. Referring now to FIG. 13B which shows a cross-sectional view of the mechanical spring actuator, it can be seen that slider 1301 has an angled feature 1317 which rests against an angled surface at the top of rod 1315. Slider 1301 is held in place by a triggering mechanism (not shown). Rod 1315 is attached to pin 1307 each end of which sits inside two angled slots 1309 (shown in FIG. 13A) of support structure 1303. When the trigger releases slider 1301, the slider moves forward forcing rod 1315 to move in a path parallel to slots 1309 due to pin 1307. Rod 1315 then impacts a sensor (not shown) supplying a high speed motive force for insertion. Toward the end of the travel of rod 1315 its angled top feature slips off of the corresponding angled feature of slider 1301 allowing the rod to return to its rest position using the force provided by return spring 1311. When slider 1301 is pulled back again, it rides along a cam surface (not shown) that directs it up out of the way of the upper end of the rod and then back down behind it again, ready for the next firing.

Figure 14:
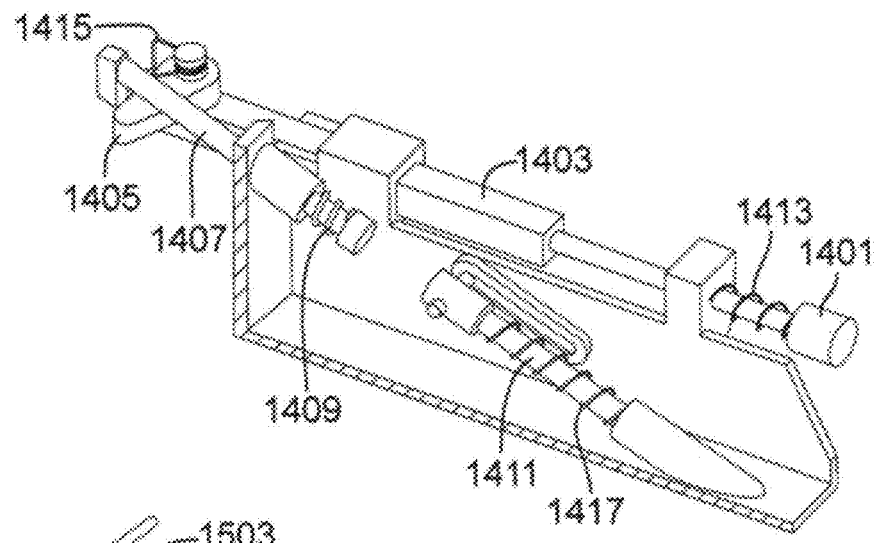
FIG. 14 shows an embodiment of the disclosure in which a series of mechanical springs and a shear member are used to control and provide a motive force to a sensor.

FIG. 14 depicts a cross-sectional view of a mechanical spring impact device employed to provide a high speed motive force to a sensor for insertion according to an embodiment. When button 1401 is pressed, trigger arm 1403 is driven forward. A small shear member 1405 at the opposite end of trigger arm 1403 is initially engaged with the top end of firing pin 1407 pulling firing pin 1407 away from rod 1411 and causing firing spring 1409 to compress and build up stored energy. As the shear moves toward the end of its travel, firing pin 1407 slips off of the shear due to the difference in the angle of their respective travel directions. At this point, firing pin 1407 travels forward with force supplied by compressed firing spring 1409 impacting rod 1411 and allowing the rod to impact a sensor (not shown) and supply a high speed motive force for insertion.

Subsequently, trigger arm 1403 proceeds back toward its rest position with force supplied by return spring 1413. Also, rod 1411 proceeds back to its rest position with force supplied by return spring 1417. As the shear member passes over the top end of firing pin 1407, the shear rotates to clear the upper end of firing pin 1407 and spring 1415 rotates the shear back into place to ready it for the next insertion.

Figure 15A:
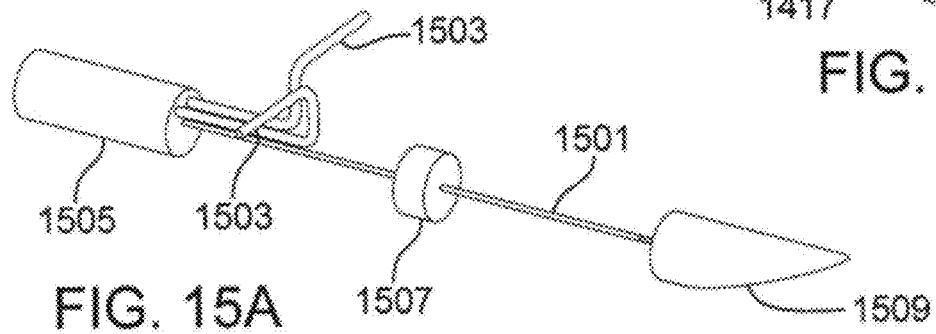
FIG. 15 shows an embodiment of the disclosure in which electrical connection is made to a sensor via wires insert molded and soldered onto the conductive regions of the sensor.
Figure 15B:
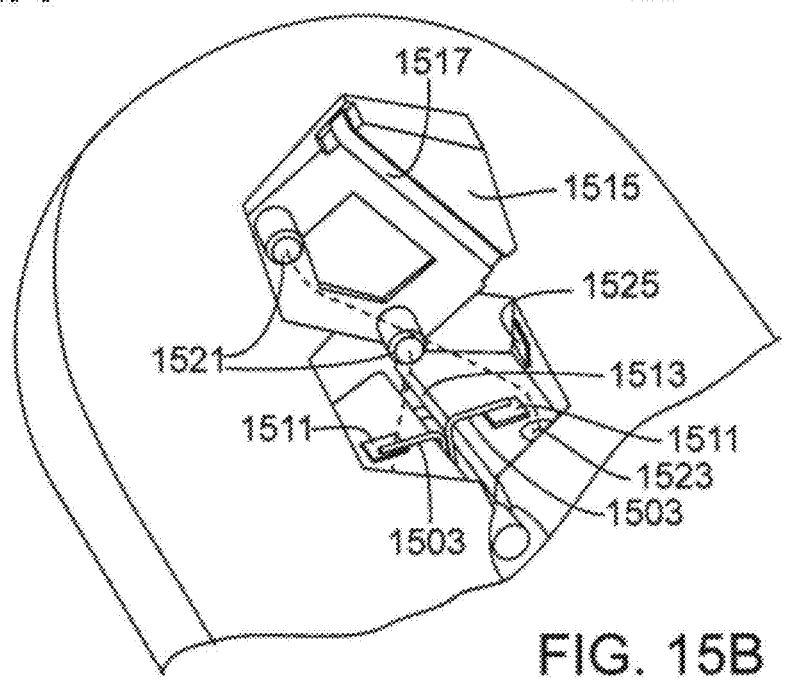

FIG. 15A depicts a wiring scheme in accordance with an embodiment of the present disclosure. Sensor 1501 is shown with plastic bottom guide 1509 and plastic center guide 1507. Lead wires 1503 are, in an embodiment, soldered to sensor 1501 and then insert-molded into top guide 1505. Referring now to FIG. 15B, the opposite ends of lead wires 1503 are soldered to contacts 1511 on the body of the device. An open groove 1513 in the guidance structure permits unobstructed movement of lead wires 1503 during sensor insertion.

Prior to insertion, pad 1515 is partially attached to the device by partially placing pins 1521 into receptacles 1523. Upon insertion of the sensor, pins 1521 are fully depressed into receptacles 1523 which cause shorting bar 1517 to contact battery pads 1525 (only one shown) as pad 1515 is pushed into its final position. In this manner, shorting bar 1517 serves to complete the power circuit of the device and turn it on.

Figure 16A:
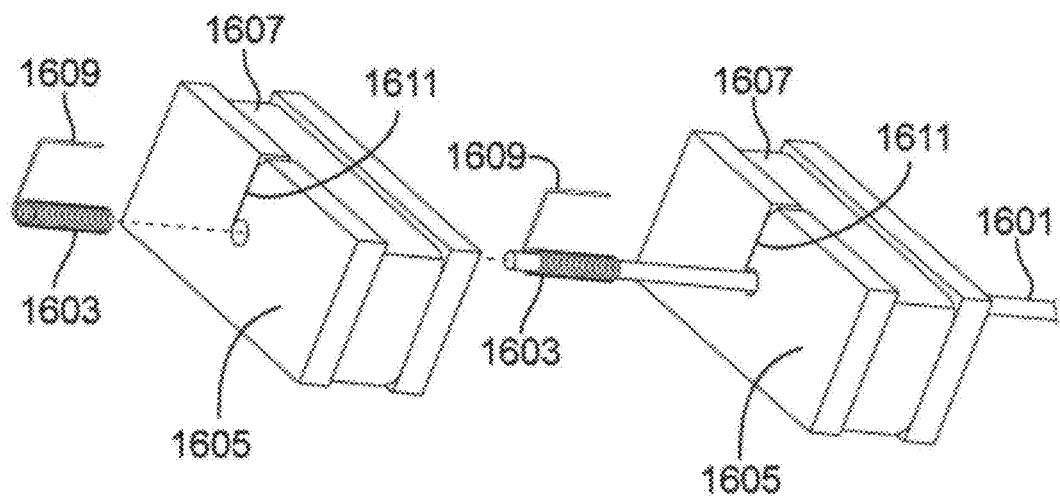
FIG. 16A shows an exploded view of an embodiment of the disclosure that utilizes a canted coil spring probe termination to make electrical contact to the sensor.
Figure 16B:
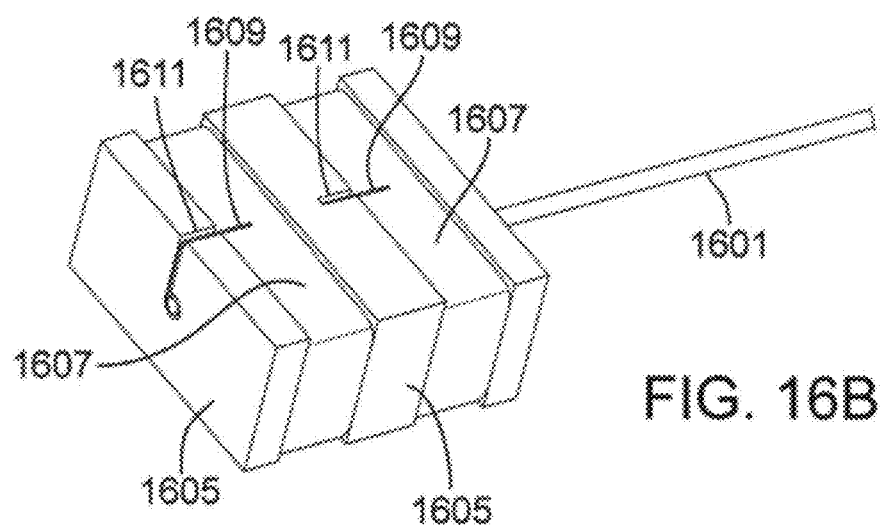
FIG. 16B depicts an assembled view of an embodiment of the disclosure that utilizes a canted coil spring probe termination to make electrical contact to the sensor.

FIGS. 16A and 16B depict a sensor electrical termination assembly in accordance with an embodiment of the present disclosure. FIG. 16A depicts an exploded view of the embodiment. Sensor 1601 is fitted with a set of canted coil springs 1603 positioned over the upper conductive regions of sensor 1601. Two small rectangular housings 1605 are positioned over the springs and two rectangular sections of sheet metal 1607 are placed into the corresponding grooves on rectangular housings 1605. Referring now to FIG. 16B, two leads 1609 extending from canted coil springs 1603 are fed through slots 1611 in rectangular housings 1605 and spot welded onto the two sections of sheet metal 1607. Upon insertion of the sensor, this termination assembly may be moved down the insertion channel (not shown). At the bottom of the insertion channel, rectangular sheet metal 1607 makes contact with two formed spring members protruding from the channel (not shown).

An alternative approach might be to reverse the orientation of the lower of the two canted coil springs so that their leads come out of the lower end of the spring. That way, the assembly is insert-molded into the rectangular housings to form a sealed connection.

Another embodiment includes pre-positioning the termination assembly at the bottom of the insertion channel. In that embodiment, a sensor travels through the assembly and make electrical contact with the springs upon insertion.

Figure 17A:
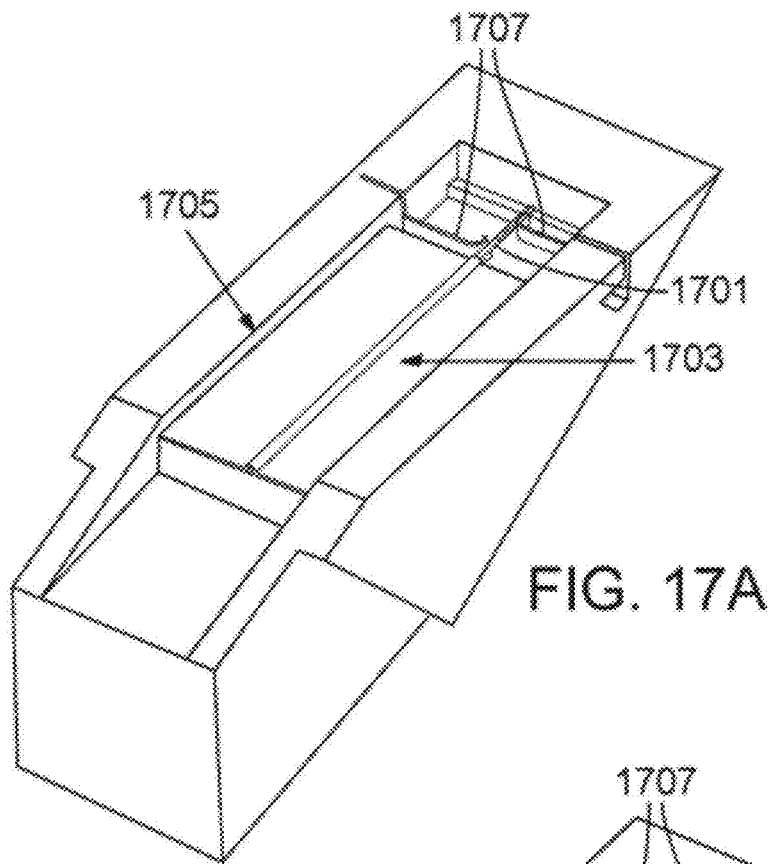
FIG. 17A shows an embodiment of the disclosure in which a paper guidance structure is utilized both to secure a sensor prior to insertion and to guide the sensor during insertion.
Figure 17B:
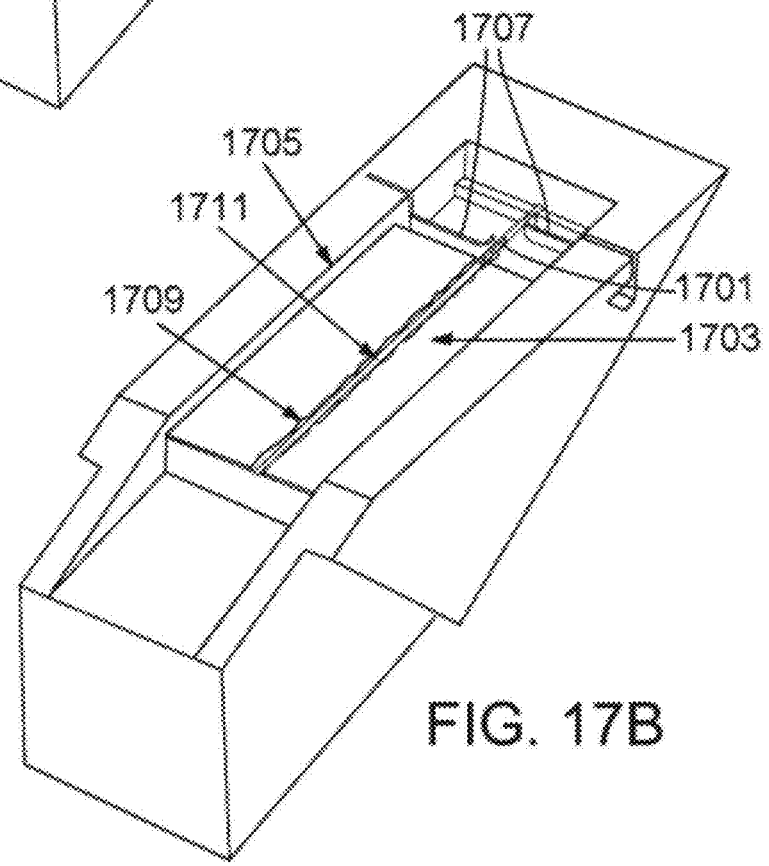
FIG. 17B shows a view of an embodiment of the disclosure after sensor insertion in which a paper guidance structure has been utilized to guide the sensor during insertion.

FIGS. 17A and 17B show a paper guidance structure in accordance with an embodiment of the present disclosure. As shown in FIG. 17A, paper 1703 is placed inside rectangular slot 1705 and above sensor 1701. Paper 1703 is used to secure paper 1703 prior to insertion and to guide sensor 1701 during insertion. Prior to insertion, sensor 1701 sits inside groove 1711 (visible in FIG. 17B) at a depth of, for example, half the diameter of sensor 1701.

Referring now to FIG. 17B, an injection activation device (not shown) pushes against the upper end of sensor 1701 and moves inside rectangular slot 1705 during insertion. As it moves, the injection activation device separates paper 1703 along slot 1711 creating paper tear 1709 as sensor 1701 is inserted. Upon insertion, the conductive regions of sensor 1701 come into contact with leaf springs 1707 electrically coupling sensor 1701 to the device.

In alternative embodiments, other similar materials can be substituted for paper such as, for example, a thin plastic covering.

In an embodiment, additional components can be housed in one or more separate modules that can be coupled to (for example, snapped to, wired to, or in wireless communication with) the insertion device. For example, the separate module may contain a memory component, a battery component, a transmitter, a receiver, a transceiver, a processor, and/or a display component, etc.

In an embodiment, a sensor with substantially uniform cross-section can be utilized. Alternatively, in an embodiment, a sensor with a varied cross section can be used. In embodiments, a sensor can be cylindrical, squared, rectangular, etc. In an embodiment, a sensor is a wire-type sensor. In an embodiment, a sensor is flexible.

For purposes of describing embodiments herein, "stiffness" is defined as the resistance of an elastic body to deflection or deformation by an external applied force. The stiffness, k, of an object may be given by Equation (1):

$$k = P/\delta \tag{1}$$

where P is the applied force and $\delta$ is the deflected distance.

For the purpose of this disclosure, flexibility is defined as the reciprocal of stiffness. Thus, "flexibility" is defined as the amount of deflection of an elastic body for a given applied force. Stiffness and flexibility are extensive material properties, meaning that they depend on properties of the material as well as shape and boundary conditions for the body being tested.

For a sensor implanted in a body, a reduction in stiffness of the sensor reduces its resistance to deflection when subjected to external forces resulting from motion of the body during various physical activities. Sensor stiffness, or resistance to external forces caused by body motion, results in pain and discomfort to the sensor user during physical activities. Accordingly, to facilitate comfort to the sensor user, the implanted sensor is designed to reduce stiffness (i.e., increase flexibility). The stiffness of an elongate cylindrical column, such as a wire, is related to the deflection of its unsupported end with applied force.

The following standard formula (Equation (2)) applies to cantilevered beams (beams supported at one end and unsupported at the other end):

$$y = W*L^3/(3E*I) \tag{2}$$

where y is the deflection, W is the applied force, L is the unsupported length, E is the modulus of elasticity (Young's modulus) of the wire material, and I is the minimum second moment of inertia. The minimum second moment of inertia (I) is related to the cross-sectional size and shape of the beam. The force (W) required for a given deflection of the wire is given by Equation (3):

$$W = 3E*I*y/L^3 \tag{3}$$

Rearranging Equation (3) and setting L=1 to normalize for a unit length of wire gives Equation (4):

$$W/y = 3EI \tag{4}$$

Using the definition of stiffness in Equation (1), and noting that W is equivalent to P and y is equivalent to $\delta$ yields Equation (5):

$$k = 3E*I \tag{5}$$

For the cylindrical wire (circular cross-section), I, the minimum second moment of inertia, is given by Equation (6):

$$I = \pi*r^4/4 \tag{6}$$

where r is the radius of the wire. Substituting the value of I of Equation (6) into Equation (5) yields Equation (7):

$$k = 3/4*\pi*E*r^4 \tag{7}$$

Equation (7) may be used to compare the stiffness of unit length of cylindrical wires of varying radius and material properties. Note that stiffness increases as the 4th power of the radius of the wire. Stiffness also increases as the modulus of elasticity for the wire material increases.

Therefore, to reduce stiffness of the wire-based sensor and improve comfort, the radius of the sensor wire can be reduced and/or a material with a lower elastic modulus can be employed for the sensor wire.

The elastic modulus (E) for several common metals is shown in the following Table 1 (in Newtons/m$^2$*10$^9$, commonly abbreviated as GPa):

TABLE 1

| Material | E in units of GPa (N/m$^2$ * 10$^9$) |
|---|---|
| Steel | 186 |
| Silver | 72 |
| Tantalum | 186 |
| Copper | 117 |
| Aluminum | 69 |
| Platinum | 145 |

In an exemplary embodiment, the wire is made of platinum-clad tantalum. Accordingly, the wire may have an elastic modulus of about 186 GPa. Tantalum is desirable because it resists fracture and/or fatigue failure when subjected to frequent bends. Also note that tantalum has an elastic modulus substantially equivalent to that of steel. Other base materials, with a lower E value, are not preferred because of the risk of fatigue and/or poor biocompatibility. Accordingly, for a given sensor material, the sensor stiffness is determined primarily by the diameter of the sensor wire base material.

In some embodiments, the radius of the wire is about 0.075 mm to about 0.125 mm (e.g., a diameter of about 0.15 mm to about 0.25 mm), such as about 0.1 mm. This yields a flexibility of about 0.707 for the 0.075 wire and 0.091 for the 0.125 mm wire in units of mm/gram-force, measured on a wire with 10 mm unsupported length. The calculations assume a bare steel or tantalum wire. The effect of any membrane coating on a wire sensor is not included in the calculations as the membrane can be very thin and its effect on flexibility is therefore negligible.

The following table, Table 2, shows the flexibility of tantalum or steel wires of various radii, for an unsupported length of 10 mm:

TABLE 2

| Wire Radius (mm) | Flexibility (mm displacement/g-force) | Stiffness (g-force/mm displacement) |
|---|---|---|
| 0.075 | 0.707 | 1.414 |
| 0.1 | 0.224 | 4.469 |
| 0.125 | 0.092 | 10.91 |
| 0.15 | 0.044 | 22.63 |
| 0.2 | 0.014 | 71.51 |

Note that the flexibility decreases and stiffness increases with the fourth power of the wire radius. The difference in flexibility for a small difference in wire radius can be substantial.

In various embodiments, the sensor has a blunt tip (e.g., as shown in FIGS. 1-4). By "blunt," it is meant that the diameter of the sensor at an end of the sensor is substantially uniform (e.g., not having a sharp point). In embodiments, the sensor wire is coated with an outer membrane to facilitate biocompatibility and/or optimize sensor performance. The coating process covers, fills, and/or softens any sharp edges of the sensor wire. Additionally, an exposed metal tip could compromise the electrochemical performance of the sensor. Furthermore, sharpening the sensor tip requires additional steps and/or complexity in the sensor manufacturing process. Accordingly, the tip of the sensor is blunt. Using methods and apparatuses described herein, the blunt-tipped sensor can be inserted into skin without the use of a trocar or other insertion device, while limiting/avoiding damage to the sensor and/or significant damage to the skin.

Inserting the blunt-tipped sensor into skin requires more pressure to be applied to the sensor than would be needed with a sharpened, rigid insertion device. For example, a motive force of about 11 to about 53 Newtons is applied to the sensor to insert the sensor into skin, or more specifically about 20 to about 22 Newtons.

In some embodiments, the relatively low stiffness and relatively high insertion pressure for the sensor increases the risk of the sensor buckling during insertion compared, for example, to a stiff, sharp needle. The behavior of the biosensor during insertion through the skin is approximated by the buckling behavior of a column subjected to a load as predicted by Euler's formula (Equation (8)):

$$Pcr = \pi^2 E \cdot I / L^2 \quad (8)$$

where E is the modulus of elasticity of the sensor material, I is the minimum second moment of inertia as defined in Equation (6) above, L is the unsupported length of the column, and Pcr is the critical buckling load.

In terms of sensor wire stiffness as defined in Equation (5), the critical buckling load is written as (Equation (9)):

$$Pcr = \pi^2 \cdot k / (3 \cdot L^2) \quad (9)$$

Therefore, the critical buckling load that is applied to the sensor wire is proportional to the sensor stiffness and inversely proportional to the square of the unsupported length of the sensor. This relationship emphasizes that a reduction in sensor wire stiffness to improve comfort during use will reduce the force that can be applied for a given unsupported sensor length during sensor insertion into the skin if buckling is to be avoided.

For a sensor having an elastic modulus of 186 GPa (e.g., a platinum clad tantalum sensor) and a radius of 0.1 mm subjected to a motive force of 22 Newtons, the buckling length calculated using Equation (9) is about 2.5 mm. The phrase "buckling length" is defined as the maximum unsupported length for a wire sensor of a given stiffness, subject to a given load (force applied axially), which will not be subject to buckling or collapse. Since the length of the sensor may be at least 12 mm inches (e.g., about 25 mm), the sensor requires a guidance structure to ensure that a maximum unsupported length of the sensor during insertion is less than the buckling length (e.g., 2.5 mm). Suitable guidance structures include the guidance structure 106 of FIG. 1, the guidance structure 303 of FIGS. 3A and 3B, the guidance structure 409 of FIG. 4 (including curved section 403), the guidance structure 601 of FIG. 6A, guides 703 and/or 705 of FIGS. 7A-7C, support structure 909 of FIG. 9A, and/or guidance structures depicted in FIGS. 10-17B.

Figure 18:
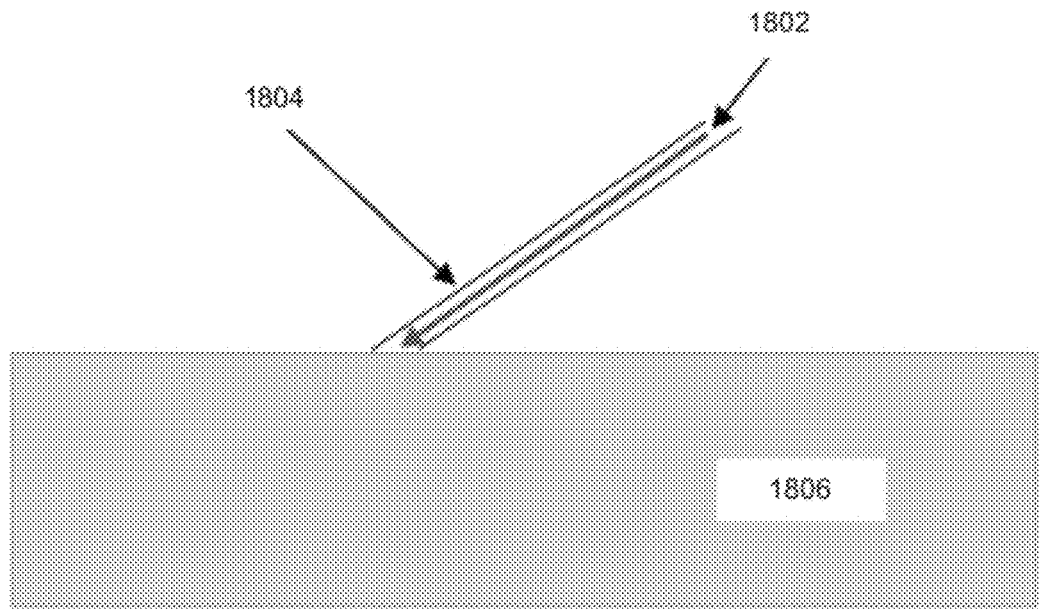
FIG. 18 shows a cross-sectional view of a sensor disposed in a coaxial guidance structure and placed on skin in accordance with an embodiment.

In some embodiments, the guidance structure includes a hollow tube that surrounds the sensor, preventing the sensor from buckling. This may be referred to as a coaxial guidance structure. The guidance structure provides support to the sensor on all sides of the sensor. FIG. 18 shows a simplified example of a sensor 1802 disposed in a coaxial guidance structure 1804 and placed on skin 1806. Another example of a coaxial guidance structure 303 is shown in FIGS. 3A and 3B.

Alternatively, the guidance structure includes an open guide channel, which includes an open, curved groove in at least a portion of the guidance structure. This type of guidance structure provides support to the sensor on only one side of the sensor over at least a portion of the length of the sensor.

The sensor is pre-stressed (compressed) by the initial insertion force and forced against the surface of the curved groove. The sensor is supported by the groove and thus unable to buckle.

Figure 19:
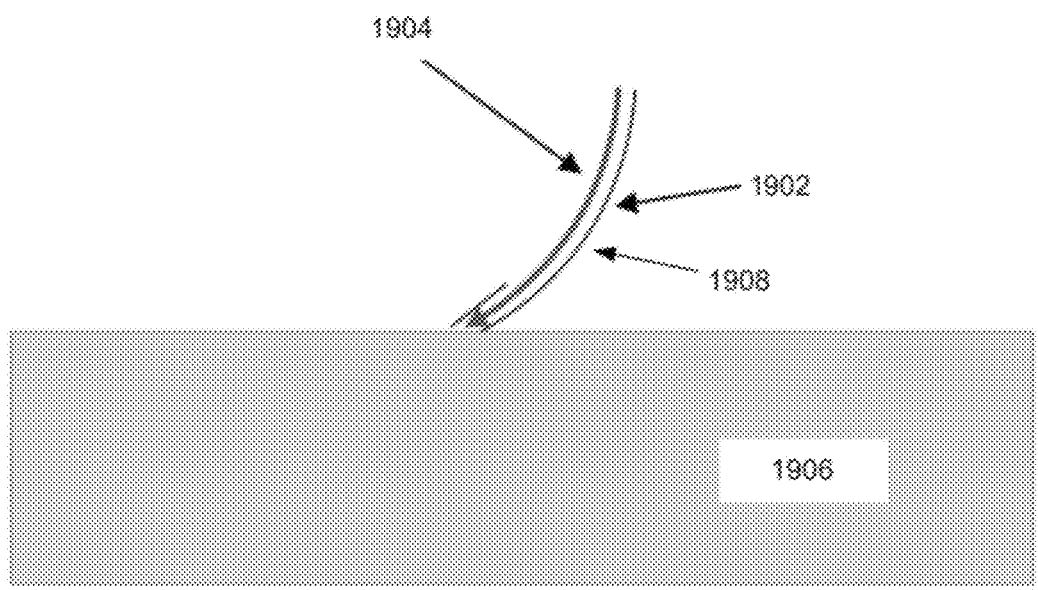
FIG. 19 shows a cross-sectional view of another embodiment in which a sensor is disposed in a coaxial guidance structure and placed on skin.

FIG. 19 shows a simplified example of a sensor 1902 disposed in a guidance structure 1904 placed on skin 1906. The guidance structure 1904 includes an open guide channel 1908. Another example of an open guide channel is the curved section 403 of guidance structure 409 shown in FIG. 4.

In various embodiments, tensioning or tightening the skin before and/or during insertion facilitates the sensor puncturing the skin and/or prevents sensor buckling. FIGS. 20A and 20B illustrate a sensor 2002 disposed in guidance structure 2004 and being inserted into skin 2006. In FIG. 20A, the skin 2006 is untensioned, while in FIG. 20B, the skin is tensioned. As shown by comparing FIG. 20A with FIG. 20B, tensioning the skin reduces the indentation of the skin from the applied force from the sensor tip (e.g., indentation of the skin until the sensor punctures the skin). In some embodiments, it is desirable to have a maximum skin indentation of less than the buckling length of the sensor (e.g., 2.5 mm as discussed above) to avoid sensor buckling. Tensioning the skin facilitates keeping the maximum skin indentation less than the buckling length.

In some embodiments, a sensor base (e.g., the sensor base 504 depicted in FIG. 5A) is disposed on the skin when the sensor is inserted into the skin. In some embodiments, the sensor base includes an adhesive patch that is coupled to the skin. The adhesive patch is less elastic than the skin and can be adhered to the skin except for a relatively small area around the insertion site. The adhesion of the adhesive patch prevents the skin from stretching, thereby limiting the indentation of the skin.

In some embodiments, the sensor insertion device includes a rounded protrusion (also referred to as a nub) around the opening in the guidance structure. The nub tensions the skin, thereby facilitating the sensor puncturing the skin and reducing the unsupported length of the sensor. Additionally, the nub deforms the skin in a way that positions the skin surface to be substantially perpendicular to the sensor insertion path when the sensor is inserted at an angle. For example, FIG. 21 illustrates a sensor 2102 being inserted by a sensor insertion device 2104 into skin 2106. A nub 2108 indents the skin 2106, thereby tensioning the skin 2106 and causing the sensor 2102 to be substantially perpendicular to the skin 2106 at the insertion site.

In various embodiments, the velocity of the sensor as it punctures the skin can be selected to facilitate puncturing the skin with the blunt tip of the sensor. The velocity of the sensor tip when it impacts the skin is important in assuring that the sensor penetrates the skin without buckling.

The momentum of the sensor facilitates skin penetration. Momentum is a function of velocity and mass. The mass of the moving parts of the sensor insertion device (e.g., the mechanism that applies the motive force to the sensor) adds to the mass of the sensor alone, thereby increasing the total moving mass and therefore the momentum.

Additionally, inertia, which is closely related to momentum, is important in determining how the skin reacts when the force of the sensor tip is applied. The skin and connected subcutaneous tissue form an elastic body which is free to move or deform when the pressure of the sensor tip is applied. However, this tissue also possesses mass. This mass causes the tissue to respond to applied forces with inertia, which limits the speed of movement and/or deformation of the skin in response to the applied force of the sensor tip. The higher the sensor velocity, the less time the skin has to move and/or deform in response to the sensor impact. Accordingly, a higher sensor velocity facilitates the sensor penetrating the skin in a substantially straight line (e.g., with minimal bending which may otherwise occur). In some embodiments, the insertion velocity contributes along with skin tensioning to preventing sensor buckling during insertion.

Figure 22A:
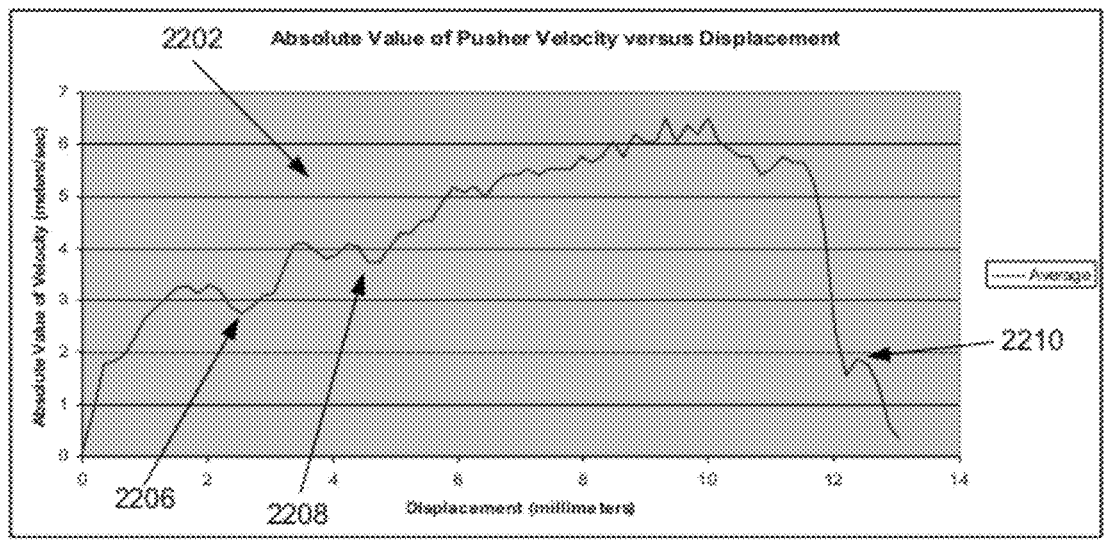
FIG. 22A shows a graph of the absolute value of pusher velocity versus displacement in accordance with an embodiment.
Figure 22B:
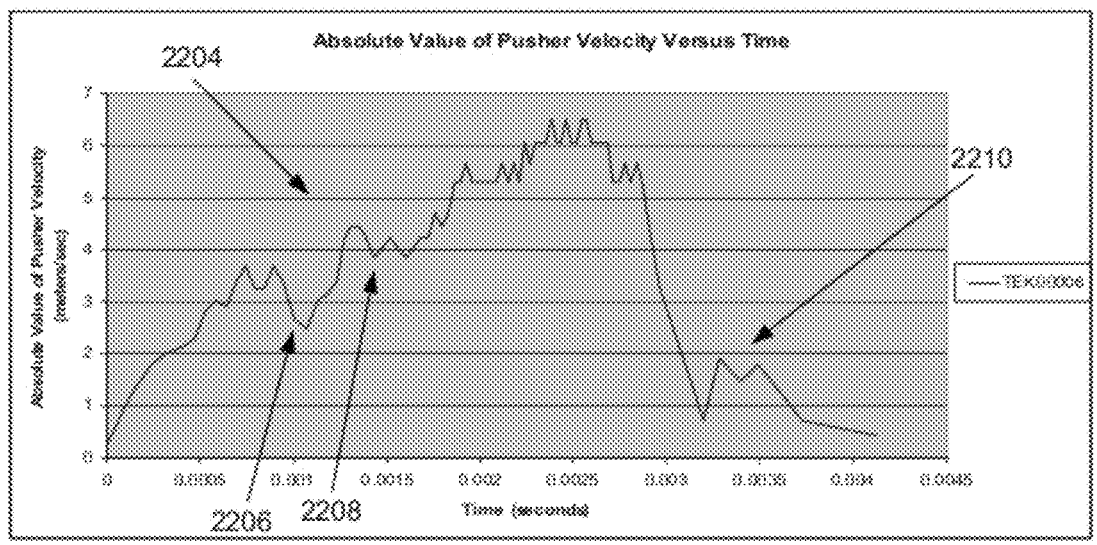
FIG. 22B shows a graph of the absolute value of pusher velocity versus time in accordance with an embodiment.

In a series of experiments, a sensor was inserted into a polymer gel "artificial skin" target using a sensor insertion device having a pusher to apply a motive force to the sensor for insertion. The velocity of the pusher was measured during insertion of the sensor into the polymer gel. The velocity of the pusher approximates the velocity of the sensor during insertion. A graph 2202 of the velocity of the pusher versus displacement (distance from initial position) is shown in FIG. 22A. A graph 2204 of the velocity of the pusher versus time is shown in FIG. 22B. Note that the velocity shown in the graphs of FIGS. 22A-B is an absolute value. Accordingly, a negative velocity, as occurs during a rebound or "bounce" of the pusher, is shown as a positive value.

The graphs 2202 and 2204 include several repeatable features. For example, note a bump 2206 near the start of the sensor travel, at about 2.5 mm of displacement and about 0.001 seconds of time. This bump 2206 corresponds to a reduction in velocity as the sensor housing travels over a retaining ridge in the guidance structure. The retaining ridge prevents the sensor probe assembly from sliding out of its starting position during shipping and handling of the device. A second small bump 2208 at about 5 mm of displacement and about 0.0015 seconds corresponds to the puncture of the artificial skin.

A third bump 2210 at about 12.5 mm and about 0.0035 seconds is caused by a rebound or "bounce" of the pusher once the sensor is seated in the sensor base. As mentioned previously, the rebound is a negative velocity relative to the forward insertion motion, but the graphs 2202 and 2204 show only the absolute value of the velocity.

Accordingly, as shown in FIGS. 22A and 22B, the velocity of the sensor during sensor insertion is about 6.4 meters per second (m/sec). In other embodiments, the velocity of the sensor during sensor insertion is about 5 m/sec to about 15 m/sec. The momentum driving the sensor insertion, as well as the velocity of the sensor, determines the minimum successful insertion velocity. Among other factors, the momentum, determined by the mass of all the moving parts coupled to the sensor, affects the ability to the sensor to maintain its velocity when the sensor encounters the resistance of the skin.

The insertion system is designed to place the sensor at any suitable angle or range of angles relative to the surface of the skin. An insertion of the sensor perpendicular to the skin surface is preferred because an insertion force perpendicular to the skin surface minimizes any shifting of the skin beneath the sensor, flexing of the sensor, and/or risk of buckling. Additionally, a perpendicular insertion prevents the sensor from "skidding" or sliding across the skin surface instead of penetrating the skin.

However, a typical wire glucose sensor functions best with a penetration of 12 millimeters (mm) or more. In relatively lean individuals, the subcutaneous tissue may be as thin as 9 mm and a vertically placed sensor penetrates beyond the subcutaneous tissue and possibly into muscle tissue. Penetration of muscle tissue can cause additional pain and discomfort for the user.

Figure 23A:
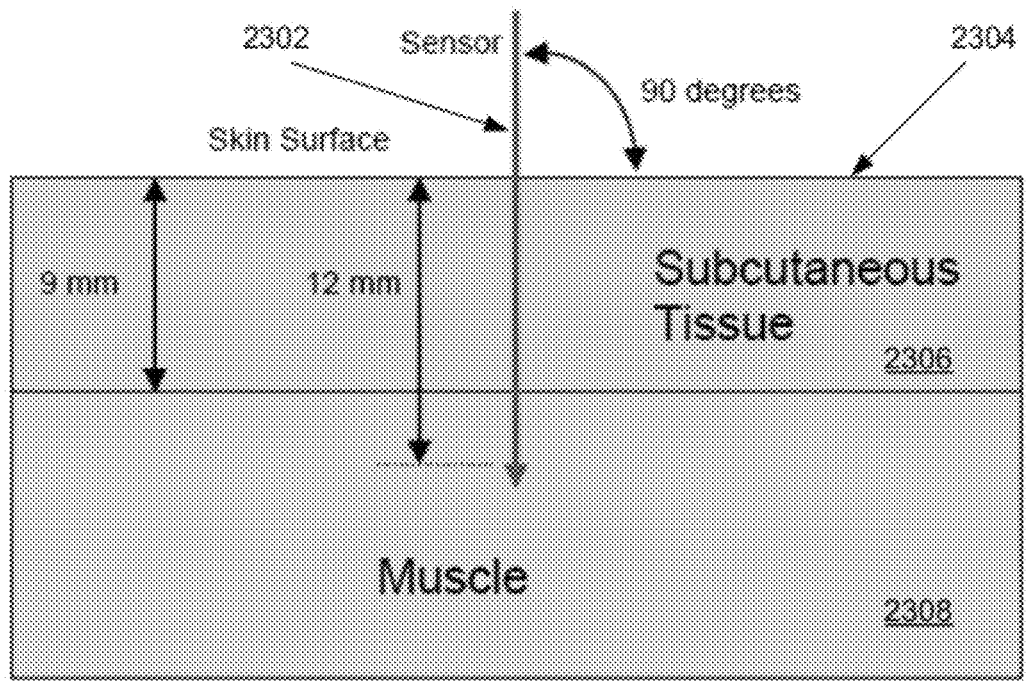
FIG. 23A shows a cross-sectional view of a sensor inserted into skin in accordance with an embodiment.

FIG. 23A shows a cross-sectional diagram of a sensor 2302 inserted vertically into a skin surface 2304. The sensor has a penetration length of 12 mm below the skin surface 2304. A subcutaneous tissue 2306 is disposed from approximately the skin surface 2302 to a depth of 9 mm. A muscle tissue 2308 is disposed below the subcutaneous tissue 2306. Accordingly, the sensor 2302 extends through the subcutaneous tissue 2306 and into muscle tissue 2308.

Figure 23B:
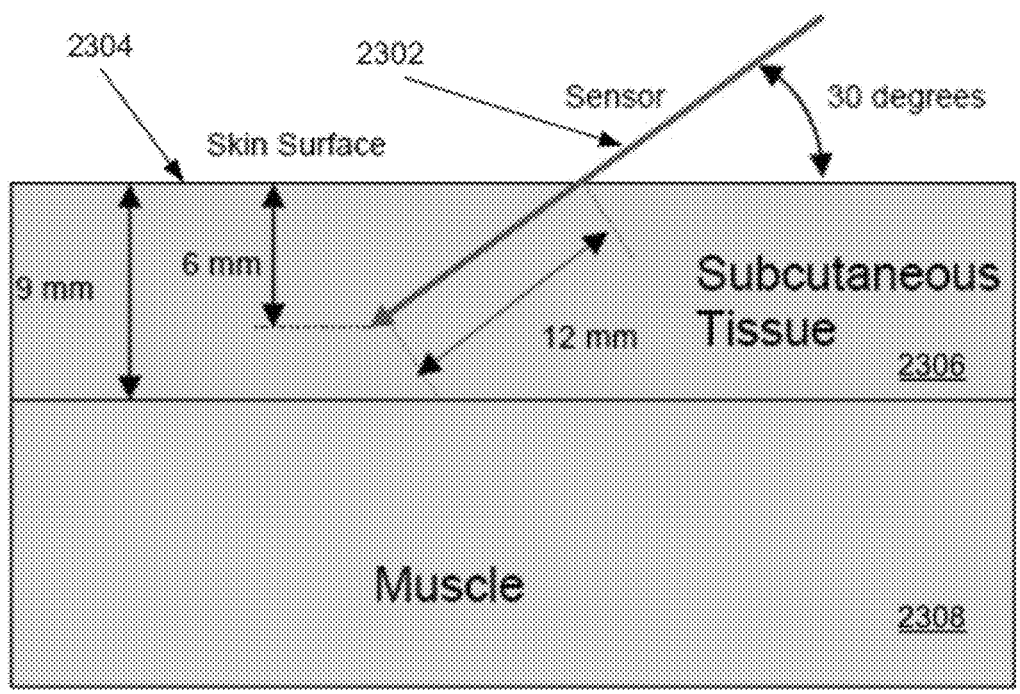
FIG. 23B shows a cross-sectional view of a sensor inserted into skin at an angle in accordance with an embodiment.

In some embodiments, the sensor is inserted at an angle of less than 90 degrees to the skin surface. This allows the desired length (e.g., 12 mm) of the sensor to be placed in subcutaneous tissue while reducing the vertical depth of the placement to assure that the entire length of the sensor remains in subcutaneous tissue. For example, FIG. 23B shows sensor 2302 inserted into the subcutaneous tissue 2306 at an angle of about 30 degrees from the plane of the skin surface 2304. This allows a length of 12 mm of the sensor to extend to a depth of approximately 6 mm in the subcutaneous tissue 2304, thereby avoiding the muscle tissue 2308.

An angle of 30 degrees may still be sufficient for penetrating the skin surface 2304 rather than sliding across the surface 2304 of the skin. Additionally, as discussed above, in some embodiments the sensor insertion device includes a nub surrounding the exit port of the guidance structure designed to deform the skin surrounding the insertion site to locally provide a skin surface 2304 that is substantially perpendicular to the sensor 2302 during insertion.

Although certain embodiments have been illustrated and described herein for purposes of description of the preferred embodiment, it will be appreciated by those of ordinary skill in the art that a wide variety of alternate and/or equivalent embodiments or implementations calculated to achieve the same purposes may be substituted for the embodiments shown and described without departing from the scope of the present disclosure. Those with skill in the art will readily appreciate that embodiments in accordance with the present disclosure may be implemented in a very wide variety of ways. This application is intended to cover any adaptations or variations of the embodiments discussed herein. Therefore, it is manifestly intended that embodiments in accordance with the present disclosure be limited only by the claims and the equivalents thereof.

What is claimed is:

1. An insertion device comprising:
    a guidance structure having an exit port and adapted to provide axial support to a flexible analyte sensor wherein the stiffness of the flexible analyte sensor is about 1.4 to about 22.6 grams-force per millimeter of deflection for an unsupported length of 10 millimeters; and
    an injection activation device associated with the guidance structure, said injection activation device having:
        a mechanism adapted to apply a high speed motive force to the flexible analyte sensor such that, when the high speed motive force is applied, the flexible analyte sensor moves at least partially through the guidance structure and at least partially passes through the exit port to cause insertion of only the flexible analyte sensor into skin; and wherein the high speed motive force is such that a velocity of the flexible analyte sensor at a time of insertion is approximately 5 meters per second to approximately 15 meters per second, wherein the guidance structure is configured so that an unsupported length of the flexible analyte sensor is less than a buckling length of the flexible analyte sensor above which the flexible analyte sensor will buckle from application of the high speed motive force, and wherein the buckling length of the flexible analyte sensor is determined by a formula $Pcr=\pi^2 *k/(3*L^2)$, wherein Pcr is a value of the high speed motive force applied to the sensor, k is a stiffness of the flexible analyte sensor, and L is the unsupported length of the flexible analyte sensor.

2. The insertion device of claim 1, wherein the velocity of the flexible analyte sensor at the time of insertion is approximately 6.4 meters per second.

3. The insertion device of claim 1, further comprising a housing having a bottom surface associated with the guidance structure, the guidance structure configured so that the flexible analyte sensor passes through the exit port at an angle from 10 to 40 degrees with respect to the bottom surface of the housing.

4. The insertion device of claim 3, further comprising a nub surrounding the exit port of the guidance structure, the nub configured to indent the skin at an insertion site such that the flexible analyte sensor is inserted into the skin at an angle that is substantially perpendicular to a plane of a local skin surface at the insertion site.

5. The insertion device of claim 3, wherein the flexible analyte sensor is inserted with an inserted length of the sensor of at least 12 millimeters.

6. The insertion device of claim 1, wherein the high speed motive force has a value of about 11 to 53 Newtons.

7. The insertion device of claim 1, wherein the high speed motive force has a value of about 22 Newtons.

8. The insertion device of claim 1, wherein an insertion angle of the sensor with respect to a plane of the skin is from 10 to 40 degrees.

9. An insertion device comprising:
a guidance structure adapted to provide axial support to a flexible analyte sensor, the guidance structure having an exit port;
an injection activation device associated with the guidance structure, said injection activation device having:
a mechanism adapted to apply a high speed motive force to the flexible analyte sensor such that, when the high speed motive force is applied, the flexible analyte sensor moves at least partially through the guidance structure and at least partially passes through the exit port to cause insertion of only the flexible analyte sensor into skin; and
a tensioning structure configured to tension a surface of the skin so that a distance from the surface of the skin at an insertion site on the surface of the skin to the exit port is less than the buckling length of the sensor, and wherein the high speed motive force is such that a velocity of the flexible analyte sensor at a time of insertion is approximately 5 meters per second to approximately 15 meters per second, and wherein the guidance structure is configured so that an unsupported length of the flexible analyte sensor is less than a buckling length of the flexible analyte sensor above which the flexible analyte sensor will buckle from application of the high speed motive force.

10. The insertion device of claim 9, wherein the tensioning structure includes a nub surrounding the exit port of the guidance structure, the nub configured to indent the skin at an insertion site.

11. The insertion device of claim 9, wherein the tensioning structure includes an adhesive patch disposed on the surface of the skin, the adhesive patch including a hole surrounding an insertion site of the sensor.

12. The insertion device of claim 9, wherein the high speed motive force has a value of about 11 to 53 Newtons.

13. The insertion device of claim 9, wherein the high speed motive force has a value of about 22 Newtons.

14. The insertion device of claim 9, wherein an insertion angle of the sensor with respect to a plane of the skin is from 10 to 40 degrees.

15. The insertion device of claim 9, wherein the velocity of the flexible analyte sensor at the time of insertion is approximately 6.4 meters per second.

16. The insertion device of claim 9, further comprising a housing having a bottom surface associated with the guidance structure, the guidance structure configured so that the flexible analyte sensor passes through the exit port at an angle from 10 to 40 degrees with respect to the bottom surface of the housing.

17. The insertion device of claim 16, further comprising a nub surrounding the exit port of the guidance structure, the nub configured to indent the skin at an insertion site such that the flexible analyte sensor is inserted into the skin at an angle that is substantially perpendicular to a plane of a local skin surface at the insertion site.

18. The insertion device of claim 16, wherein the flexible analyte sensor is inserted with an inserted length of the sensor of at least 12 millimeters.

* * * * *